United States Patent
Murray et al.

(10) Patent No.: US 7,999,114 B2
(45) Date of Patent: Aug. 16, 2011

(54) DICYCLOALKYLCARBAMOYL UREAS AS GLUCOKINASE ACTIVATORS

(75) Inventors: Anthony Murray, Hellerup (DK); Jesper Lau, Farum (DK); Per Vedso, Vaerlose (DK); Lone Jeppesen, Virum (DK); Marit Kristiansen, Soborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/994,718

(22) PCT Filed: Jul. 7, 2006

(86) PCT No.: PCT/EP2006/064028
§ 371 (c)(1),
(2), (4) Date: Jul. 9, 2008

(87) PCT Pub. No.: WO2007/006761
PCT Pub. Date: Jan. 18, 2007

(65) Prior Publication Data
US 2008/0319028 A1    Dec. 25, 2008

Related U.S. Application Data

(60) Provisional application No. 60/698,464, filed on Jul. 12, 2005.

(30) Foreign Application Priority Data

Jul. 8, 2005 (EP) .................................. 05106283

(51) Int. Cl.
*C07D 277/00* (2006.01)
*A61K 31/425* (2006.01)
(52) U.S. Cl. ........................ 548/196; 514/369
(58) Field of Classification Search .................. 548/196; 514/369
See application file for complete search history.

(56) References Cited

U.S. PATENT DOCUMENTS

| | | |
|---|---|---|
| 3,067,250 A | 12/1962 | Oja |
| 3,152,136 A | 10/1964 | Harris et al. |
| 3,317,534 A | 5/1967 | Nitta et al. |
| 3,551,442 A | 12/1970 | Guillot et al. |
| 3,734,923 A | 5/1973 | Dowding et al. |
| 3,862,163 A | 1/1975 | Boroschewski et al. |
| 3,874,873 A | 4/1975 | Volpp et al. |
| 3,887,709 A | 6/1975 | Brzozowski et al. |
| 3,967,950 A | 7/1976 | Kano et al. |
| 4,153,710 A | 5/1979 | Brzozowski et al. |
| 4,160,833 A | 7/1979 | Diel |
| 4,174,398 A | 11/1979 | Regel et al. |
| 4,175,081 A | 11/1979 | Driscoll |
| 4,183,856 A | 1/1980 | Makisumi et al. |
| 4,241,072 A | 12/1980 | Bolhofer |
| 4,243,404 A | 1/1981 | Kruger et al. |
| 4,405,644 A | 9/1983 | Kabbe et al. |
| 4,694,004 A | 9/1987 | Nakaguti et al. |
| 4,808,722 A | 2/1989 | Henrie |
| 5,262,415 A | 11/1993 | Takemoto et al. |
| 5,371,086 A | 12/1994 | Takemoto et al. |
| 5,556,969 A | 9/1996 | Chambers et al. |
| 5,846,985 A | 12/1998 | Murugesan |
| 5,846,990 A | 12/1998 | Murugesan et al. |
| 5,849,732 A | 12/1998 | Suzuki et al. |
| 5,849,769 A | 12/1998 | Lind et al. |
| 5,891,917 A | 4/1999 | Tang et al. |
| 5,935,993 A | 8/1999 | Tang et al. |
| 6,001,860 A | 12/1999 | Hamanaka |
| 6,140,343 A | 10/2000 | DeNinno et al. |
| 6,180,635 B1 | 1/2001 | Cheshire et al. |
| 6,225,346 B1 | 5/2001 | Tang et al. |
| 6,268,384 B1 | 7/2001 | Novak et al. |
| 6,271,248 B1 | 8/2001 | Murugesan et al. |
| 6,384,220 B2 | 5/2002 | Corbett et al. |
| 6,448,290 B1 | 9/2002 | Ohuchuida et al. |
| 6,486,184 B2 | 11/2002 | Kester et al. |
| 6,489,478 B1 | 12/2002 | DeNinno et al. |
| 6,500,817 B1 | 12/2002 | Fischer et al. |
| 6,559,168 B2 | 5/2003 | Marfat et al. |
| 6,608,218 B2 | 8/2003 | Kester et al. |
| 6,720,347 B2 | 4/2004 | Rawlins et al. |
| 6,720,427 B2 | 4/2004 | Sanner et al. |
| 6,784,198 B1 | 8/2004 | Pevarello et al. |

(Continued)

FOREIGN PATENT DOCUMENTS

AU    29937    12/1972

(Continued)

OTHER PUBLICATIONS

Hcaplus 1969:444446, (Nov. 5, 1968).*
Hcaplus 1980:585914, "Acylcarbodiimides. IV. Preparation and some reactions of carbamoylcarboiimides", Goerdeler, et. al., 1980.*
Colowick, S. P., "The Hexokinases", The Enzymes, 1973, vol. 9, pp. 1-48.
Chipkin, S. R. et al., "Hormone-Fuel Interrelationships: Fed State, Starvation, and Diabetes Mellitus", Joslin's Diabetes, 1994, pp. 97-115.

(Continued)

*Primary Examiner* — Janet L Andres
*Assistant Examiner* — Heidi Reese
(74) *Attorney, Agent, or Firm* — Rosemarie R. Wilk-Orescan

(57) ABSTRACT

This invention relates to dicycloalkylcarbamoyl ureas of formula (I), which are activators of glucokinase and thus may be useful for the management, treatment, control, or adjunct treatment of diseases, where increasing glucokinase activity is beneficial.

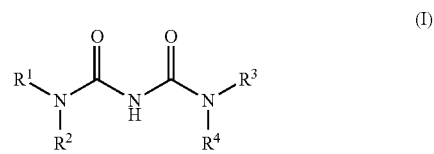

7 Claims, No Drawings

U.S. PATENT DOCUMENTS

| | | | |
|---|---|---|---|
| 6,863,647 B2 | 3/2005 | Pevarello et al. |
| 6,875,760 B2 | 4/2005 | Lau et al. |
| 6,903,125 B2 | 6/2005 | Kontani et al. |
| 6,916,814 B2 | 7/2005 | Moss et al. |
| 6,936,629 B2 | 8/2005 | Chan Chun Kong et al. |
| 7,056,942 B2 | 6/2006 | Hildesheim et al. |
| 7,196,104 B2 | 3/2007 | Askew et al. |
| 7,384,967 B2 | 6/2008 | Polisetti et al. |
| 7,582,769 B2 | 9/2009 | Murray et al. |
| 2002/0198200 A1 | 12/2002 | Kester et al. |
| 2003/0171411 A1 | 9/2003 | Kodra et al. |
| 2003/0220350 A1 | 11/2003 | Lau et al. |
| 2004/0014789 A1 | 1/2004 | Lau et al. |
| 2004/0014968 A1 | 1/2004 | Bizzarro et al. |
| 2007/0054897 A1 | 3/2007 | Murray et al. |
| 2009/0216013 A1 | 8/2009 | Murray et al. |

FOREIGN PATENT DOCUMENTS

| | | | |
|---|---|---|---|
| CA | 2416229 | | 9/2007 |
| CN | 100506807 C | | 7/2009 |
| DE | 1901501 | | 8/1969 |
| DE | 2040580 | | 4/1971 |
| DE | 2117807 | | 10/1971 |
| DE | 2129418 | | 12/1971 |
| DE | 2228890 | | 12/1972 |
| DE | 2151766 | | 4/1973 |
| DE | 2431801 | | 1/1975 |
| DE | 2264983 | | 10/1975 |
| DE | 2712630 | | 9/1978 |
| EP | 0129408 | | 12/1984 |
| EP | 0432040 | | 6/1991 |
| EP | 0885890 | | 12/1998 |
| EP | 0979823 | | 2/2000 |
| EP | 1211246 | | 6/2002 |
| EP | 1169312 | | 10/2004 |
| FR | 7.428 M | | 5/1968 |
| FR | 2001083 | | 9/1969 |
| FR | 2215967 | | 8/1974 |
| GB | 771147 | | 3/1957 |
| GB | 1185540 | * | 11/1968 |
| GB | 1185540 | | 3/1970 |
| GB | 1195672 | | 6/1970 |
| GB | 1282308 | | 7/1972 |
| GB | 1318291 | | 5/1973 |
| HU | 0200396 | | 7/2002 |
| JP | 01056660 | | 3/1989 |
| JP | 64056660 | | 3/1989 |
| JP | 4334374 | | 11/1992 |
| JP | 6-16621 | | 1/1994 |
| JP | 6102611 | | 4/1994 |
| JP | 2002-536056 | | 10/2002 |
| RU | 2021258 | | 10/1994 |
| WO | WO 91/04027 | | 4/1991 |
| WO | WO 93/24458 | | 12/1993 |
| WO | WO 94/14801 | | 7/1994 |
| WO | WO 97/24328 | | 7/1997 |
| WO | WO 99/24035 | | 5/1999 |
| WO | WO 99/24416 | | 5/1999 |
| WO | WO 99/32106 | | 7/1999 |
| WO | WO 99/32111 | | 7/1999 |
| WO | WO 99/62890 | | 12/1999 |
| WO | WO 00/17165 | | 3/2000 |
| WO | WO 00/26186 | | 5/2000 |
| WO | WO 00/26203 | | 5/2000 |
| WO | WO 00/45742 | | 8/2000 |
| WO | WO 00/53591 | | 9/2000 |
| WO | WO 00/58293 | | 10/2000 |
| WO | WO 00/58293 A3 | | 10/2000 |
| WO | WO 01/00206 | | 4/2001 |
| WO | WO 01/44216 | | 6/2001 |
| WO | WO 01/44217 | | 6/2001 |
| WO | WO 01/57008 | | 8/2001 |
| WO | WO 01/83465 | | 11/2001 |
| WO | WO 01/83478 | | 11/2001 |
| WO | WO 01/85706 A1 | | 11/2001 |
| WO | WO 01/85707 | | 11/2001 |
| WO | WO 02/08209 | | 1/2002 |
| WO | WO 02/14311 | | 2/2002 |
| WO | WO 02/46173 | | 6/2002 |
| WO | WO 02/070494 | | 9/2002 |
| WO | WO 03/055482 A1 | | 7/2003 |
| WO | WO 03/070727 | | 8/2003 |
| WO | WO 2004/002481 A1 | | 1/2004 |
| WO | WO 2004/085388 | | 10/2004 |
| WO | WO 2005/066145 | | 7/2005 |
| WO | WO 2005/103050 | | 11/2005 |
| WO | WO 2007/006814 | | 1/2007 |
| WO | WO 2008/084043 | | 7/2008 |
| WO | WO 2008/084044 | | 7/2008 |

OTHER PUBLICATIONS

Printz, R. L. et al., "Mammalian Glucokinase", Annual Review of Nutrition, 1993, vol. 13, pp. 463-496.

Meglasson, M. D. et al., "New Perspectives on Pancreatic Islet Glucokinase", American Journal of Physiology, 1984, vol. 246, pp. E1-E13.

Grupe, A. et al., "Transgenic Knockouts Reveal a Critical Requirement for Pancreatic β Cell Glucokinase in Maintaining Glucose Homeostasis", Cell, 1995, vol. 83, pp. 69-78.

Ferre, T. et al., "Evidence From Transgenic Mice that Glucokinase is Rate Limiting for Glucose Utilization in the Liver", The Faseb Journal, 1996, vol. 10, pp. 1213-1218.

Liang, Y. et al., "Variable Effects of Maturity-Onset-Diabetes-of-Youth (MODY)-associated Glucokinase Mutations on Substrate Interactions and Stability of the Enzyme", Biochem. J., 1995, vol. 309, pp. 167-173.

Glaser, B. et al., "Familial Hyperinsulinism Caused by an Activating Glucokinase Mutation", The New England Journal of Medicine, 1998, vol. 338, pp. 226-230.

Mann, G. V., "The Influence of Obesity on Health", The New England Journal of Medicine, 1974, vol. 291, pp. 226-232.

"Health Implications of Obesity", National Institutes of Health Consensus Development Conference Statement, Annals of Internal Medicine, 1985, vol. 103, pp. 147-151.

Mylari, B. L. et al., "Design and Synthesis of a Novel Family of Triazine-Based Inhibitors of Sorbitol Dehydrogenase with Oral Activity: 1-{4-[3R,5S-Dimethyl-4-(4-methyl-[1,3,5]triazin-2-yl)-piperazin-1-yl]-[1,3,5]triazin-2-yl}-(R) Ethanol", Bioorganic & Medicinal Chemistry, 2003, vol. 11, pp. 4179-4188.

Atwal et al., 1996, "Cardioselective Antiischemic ATP-Sensitive Potassium Channel Openers 4 Structure-Activity Studies on Benzopyranylcyanoguanidines: Replacement of the Benzopyran Portion," Journal of Medicinal Chemistry 39:304-313.

Castelhano et al., 2005, "Glucokinase-Activating Ureas," Bioorganic & Medicinal Chemistry Letters 15:1501-1504.

Decombe, 1932, "Acylacetic Esters," Annali Di Chimica Applicata 18:81-187.

English Translation of Decombe, 1932, "Acylacetic Esters," Annali Di Chimica Applicata 18:81-187.

Evans, et al., 1986, "Design of potent, orally effective, nonpeptidal antagonists of the peptide hormone cholecystokinin," Proceedings of the National Academy of Sciences of the United States of America, vol. 83, No. 13, Juillet 1986, USA pp. 4918-4922 (corresponds to EP0432040 in the foreign patents section).

Gardner, 1948, "The Polyoxyphenol Series III Syntheses of . . . " Canadian Journal of Research 26b:681-693.

Girard et al., 1997, Annual Review of Nutrition 17:325-352.

Grassie et al., 1950, "Preliminary Test on Possible New Stabilizers . . . " Canadian Journal of Research 28b:468-484.

Goerdeler et al., 1980, "Acylcarbodiimides. IV. Preparation and Some Reactions of Carbamoylcarboiimides," Hcaplus, Accession No. 585914.

Heitmeier et al., 1964, "Hydroxyphenethylamino Derivatives of Various Nitrogen Heterocycles," Journal of Medicinal Chemistry 7(3):288-293.

Purchase et al., 1996, "Tetrazole-Substituted Ureas as Inhibitors of Acyl-Coa:Cholesterol O-Acyltransferase (ACAT) A Novel Preparation of Ureas From Weakly Nucleophilic Amines," Bioorganic & Medicinal Chemistry Letters 6(15):1753-1758.

English Abstract of JP6016621.

Non-Final Office Action mailed Feb. 28, 2007 in U.S. Appl. No. 10/323,290 filed Dec. 19, 2002 by Kodra et al.
Final Office Action mailed Sep. 14, 2007 in U.S. Appl. No. 10/323,290 filed Dec. 19, 2002 by Kodra et al.
Final Office Action mailed Dec. 6, 2007 in U.S. Appl. No. 10/323,290 filed Dec. 19, 2002 by Kodra et al.
Non-Final Office Action mailed Apr. 1, 2008 in U.S. Appl. No. 10/323,290 filed Dec. 19, 2002 by Kodra et al.
Notice of Allowance mailed Jan. 28, 2009 in U.S. Appl. No. 10/323,290 filed Dec. 19, 2002 by Kodra et al.
Non-Final Office Action mailed May 28, 2009 in U.S. Appl. No. 10/323,290 filed Dec. 19, 2002 by Kodra et al.
Non-Final Office Action mailed Jan. 20, 2010 in U.S. Appl. No. 10/323,290 filed Dec. 19, 2002 by Kodra et al.
Notice of Allowance mailed Oct. 28, 2005 in U.S. Appl. No. 10/679,887 filed Oct. 6, 2003 by Polisetti et al.
Notice of Allowance mailed May 17, 2006 in U.S. Appl. No. 10/679,887 filed Oct. 6, 2003 by Polisetti et al.
Notice of Allowance mailed Aug. 3, 2006 in U.S. Appl. No. 10/679,887 filed Oct. 6, 2003 by Polisetti et al.
Notice of Allowance mailed Nov. 16, 2007 in U.S. Appl. No. 10/679,887 filed Oct. 6, 2003 by Polisetti et al.
Notice of Allowance mailed Jul. 23, 2008 in U.S. Appl. No. 11/365,534 filed Mar. 1, 2006 by Polisetti et al.
Non-Final Office Action mailed Nov. 21, 2008 in U.S. Appl. No. 11/982,248 filed Oct. 31, 2007 by Polisetti et al.
Final Office Action mailed Jul. 24, 2009 in U.S. Appl. No. 11/982,248 filed Oct. 31, 2007 by Polisetti et al.
Notice of Allowance mailed Feb. 25, 2010 in U.S. Appl. No. 11/982,248 filed Oct. 31, 2007 by Polisetti et al.
Notice of Allowance mailed May 11, 2010 in U.S. Appl. No. 11/982,248 filed Oct. 31, 2007 by Polisetti et al.
Non-Final Office Action mailed Jun. 16, 2009 in U.S. Appl. No. 11/981,997 filed Oct. 31, 2007 by Polisetti et al.
Final Office Action mailed Mar. 9, 2010 in U.S. Appl. No. 11/981,997 filed Oct. 31, 2007 by Polisetti et al.
Non-Final Office Action mailed Sep. 27, 2007 in U.S. Appl. No. 11/453,330 filed Jun. 14, 2006 by Murray et al.
Notice of Allowance mailed May 9, 2008 in U.S. Appl. No. 11/453,330 filed Jun. 14, 2006 by Murray et al.
Notice of Allowance mailed Nov. 3, 2008 in U.S. Appl. No. 11/453,330 filed Jun. 14, 2006 by Murray et al.
Notice of Allowance mailed May 28, 2009 in U.S. Appl. No. 11/453,330 filed Jun. 14, 2006 by Murray et al.
Non-Final Office Action mailed Sep. 4, 2009 in U.S. Appl. No. 12/188,402 filed Aug. 8, 2008 by Murray et al.
Notice of Allowance mailed Apr. 19, 2010 in U.S. Appl. No. 12/188,402 filed Aug. 8, 2008 by Murray et al.
Notice of Allowance mailed Jan. 2, 2009 in U.S. Appl. No. 11/994,728 filed Jul. 9, 2008 by Murray et al.
Notice of Allowance mailed Apr. 7, 2009 in U.S. Appl. No. 11/994,728 filed Jul. 9, 2008 by Murray et al.
Non-Final Office Action mailed Mar. 25, 2010 in U.S. Appl. No. 11/994,862 filed Jul. 9, 2008 by Lau et al.

* cited by examiner

DICYCLOALKYLCARBAMOYL UREAS AS GLUCOKINASE ACTIVATORS

CROSS-REFERENCE TO RELATED APPLICATIONS

This application is a 35 U.S.C. §371 national stage application of International Patent Application PCT/EP2006/064028 (published as WO 2007/006761 A1), filed Jul. 7, 2006, which claims benefit of priority to European Patent Application 05106283.4, filed Jul. 8, 2005.

FIELD OF THE INVENTION

This invention relates to dicycloalkylcarbamoyl ureas that are activators of glucokinase and thus may be useful for the management, treatment, control, or adjunct treatment of diseases, where increasing glucokinase activity is beneficial.

BACKGROUND OF THE INVENTION

Glucokinase (GK) is one of four hexokinases that are found in mammals [Colowick, S. P., in The Enzymes, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. Amer. J. Physiol. 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). While mutations of the GK gene are not found in the majority of patients with type 2 diabetes, compounds that activate GK and, thereby, increase the sensitivity of the GK sensor system will still be useful in the treatment of the hyperglycemia characteristic of all type 2 diabetes. Glucokinase activators will increase the flux of glucose metabolism in β-cells and hepatocytes, which will be coupled to increased insulin secretion. Such agents would be useful for treating type II diabetes. Several GK activators are known, see, for example, US 2004/0014968 (Hofmann-La Roche Inc.) and WO 2004/002481 (Novo Nordisk A/S).

Diabetes is characterized by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin, metformin is a representative example.

Even though sulphonylureas are widely used in the treatment of NIDDM this therapy is, in most instances, not satisfactory. In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment.

Since existing forms of therapy of diabetes does not lead to sufficient glycemic control and therefore are unsatisfactory, there is a great demand for novel therapeutic approaches.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain hemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemic can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary bypass surgery annually, perioperative myocardial infarction is estimated to occur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life, and reduce overall health care costs of high risk patients.

Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exists. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal-induced gastric distension is another possible inhibitory factor. Additionally the hypothalamic centres are sensitive to catecholamines, and beta-adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

SUMMARY OF THE INVENTION

The present invention provides compounds of general formula (1)

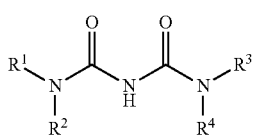

(I)

wherein the substituents are defined below, as well as further embodiments hereof described in the attached embodiments.

The present invention also provides use of the compounds of the invention for preparation of a medicament for the treatment of various diseases, e.g. for the treatment of type 2 diabetes.

Definitions

In the structural formulas given herein and throughout the present specification, the following terms have the indicated meaning:

The term "optionally substituted" as used herein means that the moiety which is optionally substituted is either unsubstituted or substituted with one or more of the substituents specified. When the moiety in question is substituted with more than one substituent, the substituent may be the same or different.

The term "adjacent" as used herein regards the relative positions of two atoms or variables, these two atoms or variables sharing a bond or one variable preceding or succeeding the other in a variable specification. By way of example, "atom A adjacent to atom B" means that the two atoms A and B share a bond.

The term "halogen" or "halo" means fluorine, chlorine, bromine or iodine.

The term "perhalomethyl" means trifluoromethyl, trichloromethyl, tribromomethyl, or triiodomethyl.

The use of prefixes of this structure: $C_{x\text{-}y}$-alkyl, $C_{x\text{-}y}$-alkenyl, $C_{x\text{-}y}$-alkynyl, $C_{x\text{-}y}$-cycloalyl or $C_{x\text{-}y}$-cycloalkyl-$C_{x\text{-}y}$-alkenyl- and the like designates radical of the designated type having from x to y carbon atoms.

The term "alkyl" as used herein, alone or in combination, refers to a straight or branched chain saturated monovalent hydrocarbon radical having from one to ten carbon atoms, for example $C_{1\text{-}8}$-alkyl or $C_{1\text{-}6}$-alkyl. Typical $C_{1\text{-}8}$-alkyl groups and $C_{1\text{-}6}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1\text{-}8}$-alkyl" as used herein also includes secondary $C_{3\text{-}8}$-alkyl and tertiary $C_{4\text{-}8}$-alkyl. The term "$C_{1\text{-}6}$-alkyl" as used herein also includes secondary $C_{3\text{-}6}$-alkyl and tertiary $C_{4\text{-}6}$-alkyl.

The term "alkenyl" as used herein, alone or in combination, refers to a straight or branched chain monovalent hydrocarbon radical containing from two to ten carbon atoms and at least one carbon-carbon double bond, for example $C_{2\text{-}8}$-alkenyl or $C_{2\text{-}6}$-alkenyl. Typical $C_{2\text{-}8}$-alkenyl groups and $C_{2\text{-}6}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "alkynyl" as used herein alone or in combination, refers to a straight or branched monovalent hydrocarbon radical containing from two to ten carbon atoms and at least one triple carbon-carbon bond, for example $C_{2\text{-}8}$-alkynyl or $C_{2\text{-}6}$-alkynyl. Typical $C_{2\text{-}8}$-alkynyl groups and $C_{2\text{-}6}$-alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "cycloalkyl" as used herein, alone or in combination, refers to a saturated mono-, bi-, or tricarbocyclic radical having from three to twelve carbon atoms, for example $C_{3\text{-}8}$-cycloalkyl. Typical $C_{3\text{-}8}$-cycloalkyl groups include, but are not limited to, cyclopropyl, cyclobutyl, cyclopentyl, cyclohexyl, cycloheptyl, cyclooctyl, bicyclo[3.2.1]octyl, bicyclo[2.2.1]heptyl, norpinyl, norbonyl, norcaryl, adamantyl and the like.

The term "cycloalkenyl" as used herein, alone or in combination, refers to an non-aromatic unsaturated mono-, bi-, or tricarbocyclic radical having from three to twelve carbon atoms, for example $C_{3\text{-}8}$-cycloalkenyl. Typical $C_{3\text{-}8}$-cycloalkyl groups include, but are not limited to cyclohexene, cycloheptene and cyclopentene, and the like.

The term "heterocyclic" or the term "heterocyclyl" as used herein, alone or in combination, refers to a saturated mono-, bi-, or tricarbocyclic group having three to twelve carbon atoms and one or two additional heteroatoms or groups selected from nitrogen, oxygen, sulphur, SO or $SO_2$, for example $C_{3\text{-}8}$-heterocyclyl. Typical $C_{3\text{-}8}$-heterocyclyl groups include, but are not limited to, tetrahydrofuryl, tetrahydrothienyl, tetrahydropyranyl, tetrahydrothiopyranyl, 1,4-dioxanyl, 1,3-dioxanyl, piperidyl, pyrrolidinyl, morpholinyl, piperazinyl, and the like.

The term "heterocycloalkenyl" as used herein, alone or in combination, refers to a non-aromatic unsaturated mono-, bi-, or tricyclic radical having from three to twelve carbon atoms, and one or two additional heteroatoms or groups selected from nitrogen, oxygen, sulphur, SO or $SO_2$, for example $C_{3-8}$-heterocycloalkenyl. Typical $C_{3-8}$-hetreocycloalkenyl groups include, but are not limited to tetrahydropyridine, azacycloheptene, 2-pyrroline, 3-pyrroline, 2-pyrazoline, imidazoline, 4H-pyran, and the like.

The term "alkoxy" as used herein, alone or in combination, refers to the monovalent radical $R^aO$—, where $R^a$ is alkyl as defined above, for example $C_{1-8}$-alkyl giving $C_{1-8}$-alkoxy. Typical $C_{1-8}$-alkoxy groups include, but are not limited to, methoxy, ethoxy, n-propoxy, isopropoxy, butoxy, sec-butoxy, tert-butoxy, pentoxy, isopentoxy, hexoxy, isohexoxy and the like.

The term "alkylthio" as used herein, alone or in combination, refers to a straight or branched monovalent radical comprising an alkyl group as described above linked through a divalent sulphur atom having its free valence bond from the sulphur atom, for example $C_{1-6}$-alkylthio. Typical $C_{1-6}$-alkylthio groups include, but are not limited to, methylthio, ethylthio, propylthio, butylthio, pentylthio, hexylthio and the like.

The term "alkoxycarbonyl" as used herein refers to the monovalent radical $R^aOC(O)$—, where $R^a$ is alkyl as described above, for example $C_{1-8}$-alkoxycarbonyl. Typical $C_{1-8}$-alkoxycarbonyl groups include, but are not limited to, methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "aryl" as used herein refers to a carbocyclic aromatic ring radical or to a aromatic ring system radical. Aryl is also intended to include the partially hydrogenated derivatives of the carbocyclic systems.

The term "heteroaryl", as used herein, alone or in combination, refers to an aromatic ring radical with for instance 5 to 7 member atoms, or to a aromatic ring system radical with for instance from 7 to 18 member atoms, containing one or more heteroatoms selected from nitrogen, oxygen, or sulphur heteroatoms, wherein N-oxides and sulphur monoxides and sulphur dioxides are permissible heteroaromatic substitutions; such as e.g. furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like. Heteroaryl is also intended to include the partially hydrogenated derivatives of the heterocyclic systems enumerated below.

Examples of "aryl" and "heteroaryl" includes, but are not limited to phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isooxazolyl (isooxazo-3-yl, isooxazo-4-yl, isooxaz-5-yl), isothiazolyl (isothiazo-3-yl, isothiazo-4-yl, isothiaz-5-yl)thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), purinyl, and tetrazolyl (5-tetrazolyl, N-tetrazolyl).

The present invention also relates to partly or fully saturated analogues of the ring systems mentioned above.

When two or more of the above defined terms are used in combination, such as in aryl-alkyl, heteroaryl-alkyl, cycloalkyl-$C_{1-6}$-alkyl and the like, it is to be understood that the first mentioned radical is a substituent on the latter mentioned radical, where the point of substitution, i.e. the point of attachment to another part of the molecule, is on the latter of the radicals, for example aryl-alkyl-:

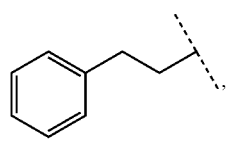

cycloalkyl-alkyl-:

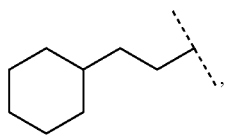

and
aryl-alkoxy-:

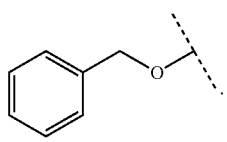

The term "fused arylcycloalkyl", as used herein, refers to an aryl group, as defined above, fused to a cycloalkyl group, as defined above and having the indicated number of carbon atoms, the aryl and cycloalkyl groups having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

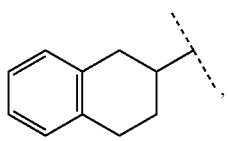

and the like.

The term "fused heteroarylcycloalkyl", as used herein, refers to a heteroaryl group, as defined above, fused to a cycloalkyl group, as defined above and having the indicated number of carbon atoms, the aryl and cycloalkyl groups having two atoms in common, and wherein the cycloalkyl group is the point of substitution. Examples of fused heteroarylcycloalkyl used herein include 6,7-dihydro-5H-cyclopenta[b]pyridine, 5,6,7,8-tetrahydroquinoline, 5,6,7,8-tetrahydroisoquinoline, 5,6,7,8-tetrahydroquinazoline and the like The term "alkylsulfanyl", as used herein, refers to the group $R^aS$—, where $R^a$ is alkyl as described above.

The term "alkylsulfenyl", as used herein, refers to the group $R^aS(O)$—, where $R^a$ is alkyl as described above.

The term "alkylsulfonyl", as used herein, refers to the group $R^aSO_2$—, where $R^a$ is alkyl as described above.

The term "alkylsulfamoyl", as used herein, refers to the group $R^aNHSO_2$—, where $R^a$ is alkyl as described above.

The term "dialkylsulfamoyl", as used herein, refers to the group $R^aR^bNSO_2$—, where $R^a$ and $R^b$ are alkyl as described above.

The term "alkylsulfinamoyl", as used herein, refers to the group $R^aNHSO$—, where $R^a$ is alkyl as described above.

The term "dialkylsulfinamoyl", as used herein, refers to the group $R^aR^bNSO$—, where $R^a$ and $R^b$ are alkyl as described above.

The term "alkylamino", as used herein, refers to the group $R^aNH$—, where $R^a$ is alkyl as described above.

The term "acyl", as used herein, refers to the group $R^aC(O)$—, where $R^a$ is alkyl, alkenyl, alkynyl, cycloalkyl, cycloalkenyl, or heterocyclyl as described above.

The term "heteroaryloxy" as used herein, alone or in combination, refers to the monovalent radical $R^aO$—, where $R^a$ is heteroaryl as defined above.

The term "aryloxycarbonyl", as used herein, refers to the group $R^a$—O—C(O)—, where $R^a$ is aryl as described above.

The term "acyloxy", as used herein, refers to the group $R^aC(O)O$—, where $R^a$ is alkyl, alkenyl, alkynyl, cycloalkyl, cycloalkenyl, or heterocyclyl as described above.

The term "aryloxy", as used herein refers to the group $R^a$—O—, where $R^a$ is aryl as described above.

The term "aroyloxy", as used herein, refers to the group $R^aC(O)O$—, where $R^a$ is aryl as described above.

The term "heteroaroyloxy", as used herein, refers to the group $R^aC(O)O$—, where $R^a$ is heteroaryl as described above.

Whenever the terms "alkyl", "cycloalkyl", "aryl", "heteroaryl" or the like or either of their prefix roots appear in a name of a substituent (e.g. arylalkoxyaryloxy) they shall be interpreted as including those limitations given above for "alkyl" and "aryl". As used herein, the term "oxo" shall refer to the substituent =O.

As used herein, the term "mercapto" shall refer to the substituent —SH.

As used herein, the term "carboxy" shall refer to the substituent —C(O)OH.

As used herein, the term "cyano" shall refer to the substituent —CN.

As used herein, the term "nitro" shall refer to the substituent —NO$_2$.

As used herein, the term "aminosulfonyl" shall refer to the substituent —SO$_2$NH$_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —S(O)$_2$—.

As used herein, the term "direct bond", where part of a structural variable specification, refers to the direct joining of the substituents flanking (preceding and succeeding) the variable taken as a "direct bond".

The term "lower", as used herein, refers to a group having between one and six carbons, and may be indicated with the prefix $C_{x-6}$—. Lower alkyl may thus be indicated as $C_{1-6}$-alkyl, while lower alkylene may be indicated as $C_{2-6}$-alkylene.

A radical such as $C_{x-y}$-cycloalkyl-$C_{a-b}$-alkenyl shall designate that the radical's point of attachment is in part of the radical mentioned last.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "attached" or "-" (e.g. —C(O)R$^{11}$ which indicates the carbonyl attachment point to the scaffold) signifies a stable covalent bond.

As used herein, the terms "contain" or "containing" can refer to in-line substitutions at any position along the above defined alkyl, alkenyl, alkynyl or cycloalkyl substituents with one or more of any of O, S, SO, SO$_2$, N, or N-alkyl, including, for example, —CH$_2$—O—CH$_2$—, —CH$_2$—SO$_2$—CH$_2$—, —CH$_2$—NH—CH$_3$ and so forth.

Certain of the above defined terms may occur more than once in the structural formulae, and upon such occurrence each term shall be defined independently of the other.

As used herein, the term "solvate" is a complex of variable stoichiometry formed by a solute (in this invention, a compound of formula (I)) and a solvent. Such solvents for the purpose of the present invention may not interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" and "treating" as used herein means the management and care of a patient for the purpose of combating a disease, disorder or condition. The term is intended to include the full spectrum of treatments for a given disorder from which the patient is suffering, such as the delaying of the progression of the disease, disorder or condition, the alleviation or relief of symptoms and complications, the prevention of the disease and/or the cure or elimination of the disease, disorder or condition. The patient to be treated is preferably a mammal, in particular a human being.

The term "pharmaceutically acceptable salt" as used herein includes pharmaceutically acceptable acid addition salts, pharmaceutically acceptable base addition salts, pharmaceutically acceptable metal salts, ammonium salts, and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, and magnesium hydroxide, in solvents such as ether, THF, methanol, t-butanol, dioxane, isopropanol, ethanol etc. Mixture of solvents may be used. Organic bases such as lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, dioxane etc. Mixture of solvents may also be used.

The term "combination therapy", "combined", "in combination with", and the like, as used herein refers to the administration of a single pharmaceutical dosage formulation which comprises the glucokinase activator compound of the present invention and another active agent(s), as well as administration of each active agent(s) in its own separate pharmaceutical dosage formulation. Where separate dosage formulations are used, the compound of the present invention and another active agent(s) can be administered to the patient at essentially the same time, i.e. concurrently, or at separate staggered times, i.e. sequentially. When given by different dosage formulations, the route of administration may be the same or different for each agent. Any route of administration known or contemplated for the individual agents is acceptable for the practice of the present invention.

DESCRIPTION OF THE INVENTION

The present invention provides compounds of formula (I)

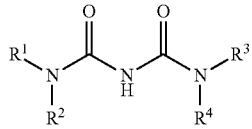

wherein $R^1$ is $C_{3-8}$-cycloalkyl, $C_{3-8}$-cycloalkenyl, $C_{3-8}$-heterocyclyl, $C_{3-8}$-heterocycloalkenyl, fused aryl-$C_{3-8}$-cycloalkyl, or fused heteroaryl-$C_{3-8}$-cycloalkyl, each of which is optionally substituted with one or more substituents $R^5$, $R^6$, $R^7$ and $R^8$;

$R^2$ is $C_{3-8}$-cycloalkyl, $C_{3-8}$-cycloalkenyl, $C_{3-8}$-heterocyclyl, $C_{3-8}$-heterocycloalkenyl, fused aryl-$C_{3-8}$-cycloalkyl or fused heteroaryl-$C_{3-8}$-cycloalkyl, each of which is optionally substituted with one or more substituents $R^9$, $R^{10}$, $R^{11}$ and $R^{12}$;

$R^3$ is hydrogen, $C_{1-6}$-alkyl, $C_{2-6}$-alkenyl, $C_{2-6}$-alkynyl, $C_{3-8}$-cycloalkyl, $C_{3-8}$-heterocyclyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy-$C_{1-6}$-alkyl, aryloxy$C_{1-6}$-alkyl, heteroaryloxy-$C_{1-6}$-alkyl $C_{3-6}$-cycloalkyl-$C_{1-6}$-alkoxy-$C_{1-6}$-alkyl, aryl-$C_{1-6}$-alkoxy-$C_{1-6}$-alkyl, heteroaryl, $C_{1-6}$-alkyl-C(O)—O—$C_{1-6}$-alkyl, $C_{1-6}$-alkylthio-$C_{1-6}$-alkyl, amino-$C_{1-6}$-alkyl, $C_{1-6}$-alkylamino-$C_{1-6}$-alkyl, di-($C_{1-6}$-alkyl)amino-$C_{1-6}$-alkyl each of which is optionally substituted with one or more substituents independently selected from $R^{20}$;

$R^4$ is hydrogen, $C_{1-6}$-alkyl, $C_{2-6}$-alkenyl, $C_{2-6}$-alkynyl, $C_{3-8}$-cycloalkyl, $C_{3-8}$-heterocyclyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy-$C_{1-6}$-alkyl, aryloxy$C_{1-6}$-alkyl, heteroaryloxy-$C_{1-6}$-alkyl $C_{3-6}$-cycloalkyl-$C_{1-6}$-alkoxy-$C_{1-6}$-alkyl, aryl-$C_{1-6}$-alkoxy-$C_{1-6}$-alkyl, heteroaryl, $C_{1-6}$-alkyl-C(O)—O—$C_{1-6}$-alkyl, $C_{1-6}$-alkylthio-$C_{1-6}$-alkyl, amino-$C_{1-6}$-alkyl, $C_{1-6}$-alkylamino-$C_{1-6}$-alkyl, di-($C_{1-6}$-alkyl)amino-$C_{1-6}$-alkyl each of which is optionally substituted with one or more substituents independently selected from $R^{21}$;

$R^5$, $R^6$, $R^7$, $R^8$, $R^9$, $R^{10}$, $R^{11}$ and $R^{12}$ are independently selected from the group consisting of halogen, nitro, cyano, hydroxy, oxo, carboxy, —$CF_3$; or —$NR^{13}R^{14}$; or $C_{1-6}$-alkyl, $C_{2-6}$-alkenyl, $C_{2-6}$-alkynyl, $C_{3-8}$-cycloalkyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, aryloxy-$C_{1-6}$-alkyl, $C_{3-6}$-cycloalkyl-$C_{1-6}$-alkoxy-$C_{1-6}$-alkyl, $C_{1-6}$-alkoxy-$C_{1-6}$-alkyl, aryl-$C_{1-6}$-alkoxy-$C_{1-6}$-alkyl, heteroaryl, heteroaryl-$C_{1-6}$-alkoxy, aryloxy, heteroaryloxy, $C_{3-6}$-cycloalkyl-$C_{1-6}$-alkylthio, $C_{1-6}$-alkyl-C(O)—O—$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl each of which is optionally substituted with one or more substituents independently selected from $R^{15}$; or —C(O)—$R^{16}$, —S(O)$_2$—$R^{16}$, —C(O)—$NR^{17}R^{18}$, —S(O)$_2$—$NR^{17}R^{18}$, —$C_{1-6}$-alkyl-C(O)—$NR^{17}R^{18}$; or $R^{13}$ and $R^{14}$ independently represent hydrogen, $C_{1-6}$-alkyl, —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —S(O)$_2$—$C_{1-6}$-alkyl, or aryl, each of which is optionally substituted with one or more halogens;

$R^{15}$ is halogen, cyano, carboxy, hydroxy, —C(O)—O—$C_{1-6}$-alkyl, —$CF_3$, $C_{1-6}$-alkyl, $C_{1-6}$-alkoxy, —$NR^{10}R^{11}$, —S(O)$_2$ $CH_3$, S(O)$_2CH_2CF_3$, —S(O)$_2CF_3$, or —S(O)$_2$ $NH_2$;

$R^{16}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryloxy-$C_{1-6}$-alkyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $R^{13}$HN—$C_{1-6}$-alkyl, $R^{13}R^{14}$—N—$C_{1-6}$-alkyl, $R^{13}R^{14}$—N—$C_{2-6}$-alkenyl, $R^{13}R^{14}$—N—S(O)$_2$—$C_{1-6}$-alkyl, $R^{13}R^{14}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl each of which is optionally substituted with one or more substituents independently selected from $R^{15}$;

$R^{17}$ and $R^{18}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{19}$; or $R^{17}$ and $R^{18}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{19}$ is halogen, cyano, hydroxy, carboxy, —$CF_3$, $C_{1-6}$-alkyl, —S(O)$_2CH_3$, or —S(O)$_2NH_2$;

$R^{20}$ and $R^{21}$ are independently selected from the group consisting of halogen, hydroxy, carboxy, oxo, carboxy-$C_{1-6}$-alkyl, hydroxy-$C_{1-6}$-alkyl, carboxy-$C_{1-6}$-alkylthio, carboxy-$C_{2-6}$-alkenylthio, carboxy-$C_{1-6}$-alkylsulfonyl, carboxy-$C_{1-6}$-alkylsulfamoyl, $C_{1-6}$-alkoxy, alkylamino, —C(O)—$C_{1-6}$-alkyl.

Another embodiment of the present invention provides compounds according to formula (I), wherein $R^1$ is $C_{3-8}$-cycloalkyl or $C_{3-8}$-heterocyclyl, each of which is optionally substituted with one or more substituents $R^5$, $R^6$, $R^7$ and $R^8$;

$R^2$ is $C_{3-8}$-cycloalkyl or $C_{3-8}$-heterocyclyl, each of which is optionally substituted with one or more substituents $R^9$, $R^{10}$, $R^{11}$ and $R^{12}$;

$R^3$ is hydrogen, $C_{1-6}$-alkyl, $C_{2-6}$-alkenyl, $C_{2-6}$-alkynyl, $C_{3-8}$-cycloalkyl, $C_{3-8}$-heterocyclyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy-$C_{1-6}$-alkyl, aryloxy$C_{1-6}$-alkyl, heteroaryloxy-$C_{1-6}$-alkyl $C_{3-6}$-cycloalkyl-$C_{1-6}$-alkoxy-$C_{1-6}$-alkyl, aryl-$C_{1-6}$-alkoxy-$C_{1-6}$-alkyl, heteroaryl, $C_{1-6}$-alkyl-C(O)—O—$C_{1-6}$-alkyl, $C_{1-6}$-alkylthio-$C_{1-6}$-alkyl, amino-$C_{1-6}$-alkyl, $C_{1-6}$-alkylamino-$C_{1-6}$-alkyl, di-($C_{1-6}$-alkyl)amino-$C_{1-6}$-alkyl each of which is optionally substituted with one or more substituents independently selected from $R^{20}$;

$R^4$ is hydrogen, $C_{1-6}$-alkyl, $C_{2-6}$-alkenyl, $C_{2-6}$-alkynyl, $C_{3-8}$-cycloalkyl, $C_{3-8}$-heterocyclyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy-$C_{1-6}$-alkyl, aryloxy$C_{1-6}$-alkyl, heteroaryloxy-$C_{1-6}$-alkyl $C_{3-6}$-cycloalkyl-$C_{1-6}$-alkoxy-$C_{1-6}$-alkyl, aryl-$C_{1-6}$-alkoxy-$C_{1-6}$-alkyl, heteroaryl, $C_{1-6}$-alkyl-C(O)—O—$C_{1-6}$-alkyl, $C_{1-6}$-alkylthio-$C_{1-6}$-alkyl, amino-$C_{1-6}$-alkyl, $C_{1-6}$-alkylamino-$C_{1-6}$-alkyl, di-($C_{1-6}$-alkyl)amino-$C_{1-6}$-alkyl each of which is optionally substituted with one or more substituents independently selected from $R^{21}$;

$R^5$, $R^6$, $R^7$, $R^8$, $R^9$, $R^{10}$, $R^{11}$ and $R^{12}$ are independently selected from the group consisting of halogen, nitro, cyano, hydroxy, oxo, carboxy, —$CF_3$; or —$NR^{13}R^{14}$; or $C_{1-6}$-alkoxy, $C_{3-6}$-cycloalkyl-$C_{1-6}$-alkoxy, aryl-$C_{1-6}$-alkoxy, aryloxy-$C_{1-6}$-alkyl, $C_{3-6}$-cycloalkyl-$C_{1-6}$-alkoxy-$C_{1-6}$-alkyl, $C_{1-6}$-alkoxy-$C_{1-6}$-alkyl, aryl-$C_{1-6}$-alkoxy-$C_{1-6}$-alkyl, heteroaryl, heteroaryl-$C_{1-6}$-alkoxy, aryloxy, heteroaryloxy, each of which is optionally substituted with one or more substituents independently selected from $R^{15}$; or —C(O)—$R^{16}$, —S(O)$_2$—$R^{16}$, —C(O)—$NR^{17}R^{18}$, —S(O)$_2$—$NR^{17}R^{18}$, —$C_{1-6}$-alkyl-C(O)—$NR^{17}R^{18}$; or $R^{13}$ and $R^{14}$ independently represent —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —S(O)$_2$—$C_{1-6}$-alkyl, each of which is optionally substituted with one or more halogens;

$R^{15}$ is halogen, carboxy, or $C_{1-6}$-alkoxy;

$R^{16}$ is $C_{1-6}$-alkyl, $C_{1-6}$-alkoxy, aryloxy-$C_{1-6}$-alkyl, carboxy-$C_{1-6}$-alkyl, carboxy-$C_{2-6}$-alkenyl, or $C_{1-6}$-alkoxy-$C_{1-6}$-alkyl, each of which is optionally substituted with one or more substituents independently selected from $R^{15}$;

$R^{17}$ and $R^{18}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{19}$; or $R^{17}$ and $R^{18}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{19}$ is halogen, cyano, hydroxy, carboxy, —CF$_3$, $C_{1-6}$-alkyl, —S(O)$_2$CH$_3$, or —S(O)$_2$NH$_2$;

$R^{20}$ and $R^{21}$ are independently selected from the group consisting of carboxy, oxo, carboxy-$C_{1-6}$-alkyl, hydroxy-$C_{1-6}$-alkyl, carboxy-$C_{1-6}$-alkylthio, carboxy-$C_{2-6}$-alkenylthio, carboxy-$C_{1-6}$-alkylsulfonyl, carboxy-$C_{1-6}$-alkylsulfamoyl, $C_{1-6}$-alkoxy, alkylamino, —C(O)—$C_{1-6}$-alkyl;

or a pharmaceutically acceptable salt thereof.

Another embodiment of the present invention provides compounds according to formula (I), wherein $R^1$ is cyclopentyl, cyclohexyl, cycloheptyl, or piperidinyl, each of which is optionally substituted with one or more substituents $R^5$, $R^6$, $R^7$ and $R^8$;

$R^2$ is cyclopentyl, cyclohexyl, cycloheptyl, or piperidinyl, each of which is optionally substituted with one or more substituents $R^9$, $R^{10}$, $R^{11}$ and $R^{12}$;

$R^3$ is hydrogen, $C_{1-6}$-alkyl, $C_{3-8}$-cycloalkyl, $C_{3-8}$-heterocyclyl, aryl, aryl-$C_{1-6}$-alkyl, heteroaryl-$C_{1-6}$-alkyl, heteroaryloxy-$C_{1-6}$-alkyl, heteroaryl, or $C_{1-6}$-alkylthio-$C_{1-6}$-alkyl, each of which is optionally substituted with one or more substituents independently selected from $R^{20}$;

$R^4$ is hydrogen, $C_{1-6}$-alkyl, $C_{3-8}$-cycloalkyl, $C_{3-8}$-heterocyclyl, aryl, aryl-$C_{1-6}$-alkyl, heteroaryl-$C_{1-6}$-alkyl, heteroaryloxy-$C_{1-6}$-alkyl, heteroaryl, or $C_{1-6}$-alkylthio-$C_{1-6}$-alkyl, each of which is optionally substituted with one or more substituents independently selected from $R^{21}$;

$R^5$, $R^6$, $R^7$, $R^8$, $R^9$, $R^{10}$, $R^{11}$ and $R^{12}$ are independently selected from the group consisting of halogen, nitro, cyano, hydroxy, oxo, carboxy, —CF$_3$; or —$NR^{13}R^{14}$; or $C_{1-6}$-alkoxy, $C_{3-6}$-cycloalkyl-$C_{1-6}$-alkoxy, aryl-$C_{1-6}$-alkoxy, aryloxy-$C_{1-6}$-alkyl, $C_{3-6}$-cycloalkyl-$C_{1-6}$-alkoxy-$C_{1-6}$-alkyl, $C_{1-6}$-alkoxy-$C_{1-6}$-alkyl, aryl-$C_{1-6}$-alkoxy-$C_{1-6}$-alkyl, heteroaryl, heteroaryl-$C_{1-6}$-alkoxy, aryloxy, heteroaryloxy, each of which is optionally substituted with one or more substituents independently selected from $R^{15}$; or —C(O)—$R^{16}$, —S(O)$_2$—$R^{16}$, —C(O)—$NR^{17}R^{18}$, —S(O)$_2$—$NR^{17}R^{18}$, —$C_{1-6}$-alkyl-C(O)—$NR^{17}R^{18}$; or $R^{13}$ and $R^{14}$ independently represent —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —S(O)$_2$—$C_{1-6}$-alkyl, each of which is optionally substituted with one or more halogens;

$R^{15}$ is halogen, carboxy, or $C_{1-6}$-alkoxy;

$R^{16}$ is $C_{1-6}$-alkyl, $C_{1-6}$-alkoxy, aryloxy-$C_{1-6}$-alkyl, carboxy-$C_{1-6}$-alkyl, carboxy-$C_{2-6}$-alkenyl, or $C_{1-6}$-alkoxy-$C_{1-6}$-alkyl, each of which is optionally substituted with one or more substituents independently selected from $R^{15}$;

$R^{17}$ and $R^{18}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{19}$; or $R^{17}$ and $R^{18}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{19}$ is halogen, cyano, hydroxy, carboxy, —CF$_3$, $C_{1-6}$-alkyl, —S(O)$_2$CH$_3$, or —S(O)$_2$NH$_2$;

$R^{20}$ and $R^{21}$ are independently selected from the group consisting of carboxy, oxo, carboxy$C_{1-6}$-alkyl, hydroxy-$C_{1-6}$-alkyl, carboxy-$C_{1-6}$-alkylthio, carboxy-$C_{2-6}$-alkenylthio, carboxy-$C_{1-6}$-alkylsulfonyl, carboxy-$C_{1-6}$-alkylsulfamoyl, $C_{1-6}$-alkoxy, alkylamino, —C(O)—$C_{1-6}$-alkyl;

or a pharmaceutically acceptable salt thereof.

In another embodiment, the present invention provides a novel compound wherein the compound is selected from the following:

1,1-Bis-(cyclohexyl)-5-methyl biuret;
1,1-Bis-(cyclohexyl)-5-butyl biuret;
1,1-Bis-(cyclohexyl)-5-(3-pyridylmethyl) biuret;
1,1-Bis-(cyclohexyl)-5-(4-fluorobenzyl) biuret;
1,1-Bis-(cyclohexyl)-5-(3-chlorobenzyl) biuret;
1,1-Bis-(cyclohexyl)-5-(o-tolyl) biuret;
1,1-Bis-(cyclohexyl)-5-(2,2,2-trifluoroethyl) biuret;
1,1-Bis-(cyclohexyl)-5-(2-thiazolyl) biuret;
1,1-Bis-(cyclohexyl)-5-ethyl biuret;
1,1-Bis-(cyclohexyl)-5-cyclohexyl biuret;
1,1-Bis-(cyclohexyl)-5-(2-pyridylmethyl) biuret;
1,1-Bis-(cyclohexyl)-5-(4-methoxybenzyl) biuret; and
1,1-Bis-(cyclohexyl)-5-(2-pyridyl) biuret;

or a pharmaceutically acceptable salt thereof.

In another embodiment, the present invention provides a novel pharmaceutical composition, comprising: a pharmaceutically acceptable carrier and a compound of the present invention, or a pharmaceutically acceptable salt thereof.

In another embodiment, the present invention provides a novel method of treating type 2 diabetes, comprising: administering to a subject in need thereof a therapeutically effective amount of a compound of the present invention.

In one aspect the invention provides a method of preventing hypoglycemia comprising administration of a compound according to the present invention.

In another aspect the invention provides the use of a compound according to the present invention for the preparation of a medicament for the prevention of hypoglycemia.

In another aspect the invention provides a compound as described herein, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

In another aspect the invention provides a compound as described herein for use as a medicament.

In another aspect the invention provides a compound as described herein for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food intake, for appetite regulation, for regulating feeding behaviour, or for enhancing the secretion of enteroincretins, such as GLP-1.

In another aspect the invention provides a pharmaceutical composition comprising, as an active ingredient, at least one compound as described herein together with one or more pharmaceutically acceptable carriers or excipients.

In one embodiment such a pharmaceutical composition may be in unit dosage form, comprising from about 0.05 mg to about 1000 mg, preferably from about 0.1 mg to about 500 mg and especially preferred from about 0.5 mg to about 200 mg of the compound according to the present invention.

In another aspect the invention provides the use of a compound according to the invention for increasing the activity of glucokinase.

In another aspect the invention provides the use of a compound according to the invention for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behaviour, or for enhancing the secretion of enteroincretins. In another aspect the invention provides the use of a compound according to the invention for the preparation of a medicament for the adjuvant treatment of type 1 diabetes for preventing the onset of diabetic complications.

In another aspect the invention provides the use of a compound according to the invention for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

In one embodiment the invention provides any of the above uses in a regimen which comprises treatment with a further antidiabetic agent.

In a further aspect the invention provides the use of a compound according to the invention or a pharmaceutical composition as described above for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behaviour, or for enhancing the secretion of enteroincretins.

In a further aspect the invention provides the use of a compound according to the invention or a pharmaceutical composition as described above for the adjuvant treatment of type 1 diabetes for preventing the onset of diabetic complications.

In a further aspect the invention provides the use of a compound according to the invention or a pharmaceutical composition as described above for increasing the number and/or the size of beta cells in a mammalian subject, for treatment of beta cell degeneration, in particular apoptosis of beta cells, or for treatment of functional dyspepsia, in particular irritable bowel syndrome.

In another embodiment the invention provides a for the treatment of a glucokinase-deficiency mediated condition/disease which is caused by a glucokinase mutation.

In another embodiment the invention provides a method wherein the glucokinase-deficiency mediated condition/disease is Maturity-Onset Diabetes of the Young, Neonatal Diabetes Mellitus, or Persistent Neonatal Diabetes Mellitus.

In another embodiment the invention provides a method for preventing or ameliorating the development of diabetes in subjects exhibiting symptoms of Impaired Glucose Tolerance, Gestational Diabetes Mellitus, Polycystic Ovarian Syndrome, Cushings syndrome or Metabolic Syndrome comprising administering to a subject in need of such treatment a compound according to the invention or pharmaceutical composition thereof, wherein blood glucose normalization occurs with reduced risk of hypoglycemia.

In another embodiment the invention provides a method for preventing or ameliorating microvascular diseases comprising administering to a subject in need of such treatment a compound according to the invention or pharmaceutical composition thereof.

In another embodiment the invention provides a method for preventing macrovascular diseases in subjects exhibiting symptoms of Impaired Glucose Tolerance, Gestational Diabetes Mellitus, or Metabolic Syndrome, comprising administering to a subject in need of such treatment a compound according to the invention or pharmaceutical composition thereof, alone or in combination with lipid-lowering drugs, wherein blood glucose normalization occurs with reduced risk of hypoglycemia.

In another embodiment the invention provides a method for the preservation of beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method for preventing amyloid beta peptide induced cell death comprising administering to a subject in need of such treatment a compound according to the invention or pharmaceutical composition thereof, wherein blood glucose normalization occurs with reduced risk of hypoglycemia.

In another embodiment the invention provides a method wherein the subject is a veterinary subject.

In another embodiment the invention provides a method wherein a compound according to the invention is administered as a food additive.

In another embodiment the invention provides a method for the treatment of hepatic conditions benefiting from blood glucose normalization comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions benefiting from improved liver function comprising administering to a subject in need of such treatment a compound according to the invention or pharmaceutical composition thereof.

In another embodiment the invention provides a method for the treatment of hyperglycemic conditions that result from critical illness, or as a consequence of therapeutic intervention comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions that result from critical illness like cancer, or are a consequence of therapy, for example cancer therapy or HIV-treatment, comprising administering to a subject in need of such treatment a compound according to the invention or pharmaceutical composition thereof.

In another embodiment the invention provides a method of treatment adjuvant to insulin in insulin-requiring diabetes type 2, or as replacement for insulin comprising administering to a subject in need of such treatment a compound according to the invention or pharmaceutical composition thereof, wherein blood glucose normalization occurs with reduced risk of hypoglycemia.

In another embodiment the invention provides a method for the treatment of lipodistrophy comprising administering to a subject in need of such treatment a compound according to the invention or pharmaceutical composition thereof, wherein blood glucose normalization occurs with reduced risk of hypoglycemia.

In another embodiment the invention provides a method for the treatment of hyperglycemia resulting from severe physical stress without signs of liver failure comprising administering to a subject in need of such treatment a compound according to the invention or pharmaceutical composition thereof, wherein blood glucose normalization occurs with reduced risk of hypoglycemia.

In another embodiment the invention provides a method wherein the severe physical stress is multiple trauma, or diabetic ketoacidosis.

In another embodiment the invention provides a method for preventing apoptotic liver damage comprising administering to a subject in need of such treatment a compound according to the invention or pharmaceutical composition thereof.

In another embodiment the invention provides a method for preventing hypoglycemia comprising administering to a subject in need of such treatment a compound according to the invention or pharmaceutical composition thereof, wherein blood glucose normalization occurs with reduced risk of hypoglycemia.

In another embodiment the invention provides a method for increasing beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method of preventing type 1 diabetes comprising administering to a subject in need of such treatment a compound according to the invention or pharmaceutical composition thereof, wherein blood glucose normalization occurs with reduced risk of hypoglycemia.

In another embodiment the invention provides a method of preserving and/or increasing beta-cell mass and function in patients having undergone pancreatic islet transplantation comprising administering to a subject in need of such treatment a compound according to the invention or pharmaceutical composition thereof.

In another embodiment the invention provides a method of improving glucose control during and after surgery comprising administering to a subject in need of such treatment a compound according to the invention or pharmaceutical composition thereof.

In another embodiment the invention provides a method of improving liver function and/or survival in patients undergoing liver transplantation comprising administering to a subject in need of such treatment a compound according to the invention or pharmaceutical composition thereof. In another embodiment hereof the invention provides a method wherein the administration occurs before, during or after transplantation, or any combination thereof.

In another embodiment the invention provides a method of obtaining blood glucose normalization comprising administering to a subject in need of such treatment a compound according to the invention or pharmaceutical composition thereof, wherein blood glucose normalization occurs with reduced risk of hypoglycemia.

In another embodiment the invention provides a method of preventing or ameliorating diabetic late complications comprising administering to a subject in need of such treatment a compound according to the invention or pharmaceutical composition thereof.

In another embodiment the invention provides a method of treating type 1 or 2 diabetes comprising administering to a subject in need of such treatment a compound according to the invention or pharmaceutical composition thereof, wherein the treatment does not result in a weight gain.

In another embodiment the invention provides a method of preventing diabetic ketoacidosis comprising administering to a subject in need of such treatment a compound according to the invention or pharmaceutical composition thereof.

In another embodiment, the present invention provides a novel method of treating a condition or disorder, comprising: administering to a subject in need thereof a therapeutically effective amount of a compound of the present invention, wherein the condition or disorder is selected from a metabolic disorder, blood glucose lowering, hyperglycemia, impaired glucose tolerance (IGT), Syndrome X, Polycystic Ovarian Syndrome, impaired fasting glucose (IFG), type I diabetes, delaying the progression of impaired glucose tolerance (IGT) to type II diabetes, delaying the progression of non-insulin requiring type II diabetes to insulin requiring type II diabetes, dyslipidemia, hyperlipidemia, hypertension, treatment or prophylaxis of obesity, lowering of food intake, appetite regulation, regulating feeding behaviour, and enhancing the secretion of enteroincretins.

In a further aspect of the present invention the present compounds are administered in combination with one or more further active substances in any suitable ratios. When used in combination with one or more further active substances, the combination of compounds is preferably a synergistic combination. Synergy occurs when the effect of the compounds when administered in combination is greater than the additive effect of the compounds when administered as a single agent. In general, a synergistic effect is most clearly demonstrated at sub-optimal concentrations of the compounds. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferatoractivated receptor) and RXR (retinoid X receptor) agonists such as ALRT-268, LG-1268 or LG-1069.

In one embodiment of the present invention, the present compounds are administered in combination with a sulphonylurea eg tolbutamide, chlorpropamide, tolazamide, glibenclamide, glipizide, glimepiride, glicazide or glyburide.

In one embodiment of the present invention, the present compounds are administered in combination with a biguanide eg metformin.

In one embodiment of the present invention, the present compounds are administered in combination with a meglitinide eg repaglinide or senaglinide/nateglinide.

In one embodiment of the present invention, the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one embodiment of the present invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one embodiment of the present invention the present compounds are administered in combination with an α-glucosidase inhibitor eg voglibose, emiglitate, miglitol or acarbose.

In one embodiment of the present invention the present compounds are administered in combination with a glycogen phosphorylase inhibitor eg the compounds described in WO 97/09040 (Novo Nordisk A/S).

In one embodiment of the present invention the present compounds are administered in combination with an agent acting on the ATP-dependent potassium channel of the pancreatic β-cells eg tolbutamide, glibenclamide, glipizide, glicazide, BTS-67582 or repaglinide.

In one embodiment of the present invention the present compounds are administered in combination with nateglinide.

In one embodiment of the present invention the present compounds are administered in combination with an antihyperlipidemic agent or a antilipidemic agent eg cholestyramine, colestipol, clofibrate, gemfibrozil, lovastatin, pravastatin, simvastatin, probucol or dextrothyroxine.

Furthermore, the compounds according to the invention may be administered in combination with one or more anti-obesity agents or appetite regulating agents. Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further antiobesity agents are bupropion (antidepressant), topiramate (anticonvulsant), ecopipam (dopamine D1/D5 antagonist) and naltrexone (opioid antagonist).

In one embodiment of the present invention the antiobesity agent is leptin.

In one embodiment of the present invention the antiobesity agent is a serotonin and norepinephrine reuptake inhibitor eg sibutramine.

In one embodiment of the present invention the antiobesity agent is a lipase inhibitor eg orlistat.

In one embodiment of the present invention the antiobesity agent is an adrenergic CNS stimulating agent eg dexamphetamine, amphetamine, phentermine, mazindol phendimetrazine, diethylpropion, fenfluramine or dexfenfluramine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In one embodiment of the present invention, the present compounds are administered in combination with insulin, insulin derivatives or insulin analogues.

In one embodiment of the invention the insulin is an insulin derivative is selected from the group consisting of B29-N$^\epsilon$-myristoyl-des(B30) human insulin, B29-N$^\epsilon$-palmitoylides (B30) human insulin, B29-N$^\epsilon$-myristoyl human insulin, B29-N$^\epsilon$-palmitoyl human insulin, B28-N$^\epsilon$-myristoyl LyS$^{B28}$ Pro$^{B29}$ human insulin, B28-N$^\epsilon$-palmitoyl LyS$^{B28}$ Pro$^{B29}$ human insulin, B30-N$^\epsilon$-myristoyl-Thr$^{B29}$LyS$^{B30}$ human insulin, B30-N$^\epsilon$-palmitoyl-Thr$^{B29}$LyS$^{B30}$ human insulin, B29-N$^\epsilon$-(N-palmitoyl-$\gamma$-glutamyl)-des(B30) human insulin, B29-N$^\epsilon$-(N-lithocholyl-$\gamma$-glutamyl)des(B30) human insulin, B29-N$^\epsilon$-($\omega$-carboxyheptadecanoyl)-des(B30) human insulin and B29-N$^\epsilon$-($\omega$-carboxyheptadecanoyl) human insulin.

In another embodiment of the invention the insulin derivative is B29-N$^\epsilon$-myristoyldes(B30) human insulin.

In a further embodiment of the invention the insulin is an acid-stabilized insulin. The acid-stabilized insulin may be selected from analogues of human insulin having one of the following amino acid residue substitutions:
A21G
A21G, B28K, B29P
A21G, B28D
A21G, B28E
A21G, B3K, B29E
A21G, desB27
A21G, B9E
A21G, B9D
A21G, B10E insulin.

In a further embodiment of the invention the insulin is an insulin analogue. The insulin analogue may be selected from the group consisting of: An analogue wherein position B28 is Asp, Lys, Leu, Val, or Ala and position B29 is Lys or Pro; and des(B28-B30), des(B27) or des(B30) human insulin.

In another embodiment the analogue is an analogue of human insulin wherein position B28 is Asp or Lys, and position B29 is Lys or Pro.

In another embodiment the analogue is des(B30) human insulin.

In another embodiment the insulin analogue is an analogue of human insulin wherein position B28 is Asp.

In another embodiment the analogue is an analogue wherein position B3 is Lys and position B29 is Glu or Asp.

In another embodiment the GLP-1 derivative to be employed in combination with a compound of the present invention refers to GLP-1(1-37), exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1(7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1(1-37) are e.g. Met$^8$-GLP-1(7-37) wherein the alanine in position 8 has been replaced by methionine and the amino acid residues in position 1 to 6 have been deleted, and Arg$^{34}$-GLP-1(7-37), wherein the valine in position 34 has been replaced with arginine and the amino acid residues in position 1 to 6 have been deleted. An example of an insulinotropic analogue of exendin-4(1-39) is Ser$^2$Asp$^3$-exendin-4(1-39) wherein the amino acid residues in position 2 and 3 have been replaced with serine and aspartic acid, respectively (this particular analogue also being known in the art as exendin-3). Insulinotropic derivatives of GLP-1(1-37), exendin-4(1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogues thereof are GLP-1(7-36)-amide, Arg$^{34}$, Lys$^{26}$(N$^\epsilon$-($\gamma$-Glu(N$^{\alpha\text{-}hexadecanoyl}$)))-GLP-1(7-37) and Tyr$^{31}$-exendin-4(1-31)-amide. Further examples of GLP-1(1-37), exendin-4(1-39), insulinotropic fragments thereof, insulinotropic analogues thereof and insulinotropic derivatives thereof are described in WO 98/08871, WO 99/43706, U.S. Pat. No. 5,424,286 and WO 00/09666.

In another aspect of the present invention, the present compounds are administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In one embodiment of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, creams, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term pharmaceutically acceptable salts refers to non-toxic salts of the compounds of this invention which are generally prepared by reacting the free base with a suitable organic or inorganic acid or by reacting the acid with a suitable organic or inorganic base. When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further aspect of the present invention.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents. syrups and and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further embodiment, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

Core:

| | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |

*Polacrillin potassium NF, tablet disintegrant, Rohm and Haas.

Coating:

| | | |
|---|---|---|
| Hydroxypropyl methylcellulose | approx. | 9 mg |
| Mywacett 9-40 T** | approx. | 0.9 mg |

**Acylated monoglyceride used as plasticizer for film coating.

If desired, the pharmaceutical composition of the present invention may comprise a compound according to the present invention in combination with further active substances such as those described in the foregoing.

The present invention also provides a method for the synthesis of compounds useful as intermediates in the preparation of compounds of formula (I) along with methods for the preparation of compounds of formula (I). The compounds can be prepared readily according to the following reaction Schemes (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

Pharmacological Methods

Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM $MgCl_2$, 2 mM dithiothreitol, 0.6 mM NADP, 1 mM ATP, 0.195 µM G-6-P dehydrogenase (from Roche, 127 671), 15 nM recombinant human glucokinase. The glucokinase is human liver glucokinase N-terminally truncated with an N-terminal His-tag (($His)_8$-VEQILA . . . Q466) and is expressed in E. coli as a soluble protein with enzymatic activity comparable to liver extracted GK.

The purification of His-tagged human glucokinase (hGK) was performed as follows: The cell pellet from 50 ml E. coli culture was resuspended in 5 ml extraction buffer A (25 mM HEPES, pH 8.0, 1 mM $MgCl_2$, 150 mM NaCl, 2 mM mercaptoethanol) with addition of 0.25 mg/ml lysozyme and 50 µg/ml sodium azide. After 5 minutes at room temperature 5 ml of extraction buffer B (1.5 M NaCl, 100 mM $CaCl_2$, 100 mM $MgCl_2$, 0.02 mg/ml DNase 1, protease inhibitor tablet (Complete® 1697498): 1 tablet pr. 20 ml buffer) was added. The extract was then centrifugated at 15.000 g for 30 minutes. The resulting supernatant was loaded on a 1 ml Metal Chelate Affinity Chromatography (MCAC) Column charged with $Ni^{2+}$. The column is washed with 2 volumes buffer A containing 20 mM imidazole and the bound his-tagged hGK is subsequently eluted using a 20 minute gradient of 20 to 500 mM imididazol in buffer A. Fractions are examined using SDS-gel-electrophoresis, and fractions containing hGK (MW: 52 KDa) are pooled. Finally a gelfiltration step is used for final polishing and buffer exhange. hGK containing fractions are loaded onto a Superdex 75 (16/60) gelfiltration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 ml E. coli culture is generally approximately 2-3 mg hGK with a purity >90%.

The compound to be tested is added into the well in final 2.5% DMSO concentration in an amount sufficient to give a desired concentration of compound, for instance 1, 5, 10, 25 or 50 µM. The reaction starts after glucose is added to a final concentration of 2, 5, 10 or 15 mM. The assay uses a 96-well UV plate and the final assay volume used is 200 µl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibit activation of glucokinase in this assay. A compound, which at a concentration of at or below 30 µM gives 1.5-fold higher glucokinase activity than the result from the assay without compound, is deemed to be an activator of glucokinase.

The glucose sensitivity of the compounds are measured at a compound concentration of 10 µM and at glucose concentrations of 5 and 15 mM.

Glucokinase Activity Assay (II)

Determination of Glycogen Deposition in Isolated Rat Hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 µM dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $Mg_2SO_4$, 1.5 mM $KH_2PO_4$, 20 mM HEPES, 9 mM $NaHCO_3$, 0.1% w/v HSA, and 2.25 mM $CaCl_2$, pH 7.4 at 37° C.) and incubated in 100 µl buffer A containing 15 mM glucose and increasing concentrations of the test compound, such as for instance 1, 5, 10, 25, 50 or 100 µM, for 180 minutes. Glycogen content is measured using standard procedures (Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)

Stimulation of Insulin Secretion by Glucokinase Activators in Ins-1E Cells

The glucose responsive β-cell line INS-1E is cultivated as described by Asfari M et al., Endocrinology, 130, 167-178 (1992). The cells are then seeded into 96 well cell culture plates and grown to a density of approximately $5\times10^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 µM, and the supernatants collected for measurements of insulin concentrations by ELISA (n=4). A compound, which when used in this assay gives an significant increase in insulin secretion in response to glucose compared to the result from the assay without compound, is deemed to have activity in this assay.

All references, including publications, patent applications, and patents, cited herein are hereby incorporated by reference to the same extent as if each reference were individually and specifically indicated to be incorporated by reference and were set forth in its entirety herein (to the maximum extent permitted by law).

Any combination of the above-described elements in all possible variations thereof is encompassed by the invention unless otherwise indicated herein or otherwise clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted and should be read as encompassing the phrases "consisting", "substantially comprised of," and "consisting essentially of" (e.g., where a disclosure of a composition "comprising" a particular ingredient is made, it should be understood that the invention also provides an otherwise identical composition characterized by, in relevant part, consisting essentially of the ingredient and (independently) a composition consisting solely of the ingredient).

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

While the invention has been described and illustrated with reference to certain preferred embodiments thereof, those skilled in the art will appreciate that various changes, modifications and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

EXAMPLES

Abbreviations used in the Schemes and Examples are as follows:
d=day(s)
g=gram(s)
h=hour(s)
MHz=mega hertz
L=liter(s)
M=molar
mg=milligram(s)
min=minute(s)
mL=milliliter(s)
mM=millimolar
mmol=millimole(s)
mol=mole(s)
N=normal
ppm=parts per million
i.v.=intravenous
m/z=mass to charge ratio
mp=melting point
MS=mass spectrometry
HPLC=high pressure liquid chromatography
HPLC-MS=high pressure liquid chromatography-mass spectrometry
NMR=nuclear magnetic resonance spectroscopy
p.o.=per oral
$R_f$=retention time
rt=room temperature
s.c.=subcutaneous
TLC=thin layer chromatography
BuOK=Potassium tert-butoxide
Boc=tert-Butyloxycarbonyl
CDI=carbonyldiimidazole
DBU=1,8-Diazabicyclo[5.4.0]-undec-7-en
DCM ($CH_2Cl_2$)=dichloromethane, methylenechloride
DHOBt=3,4-Dihydro-3-hydroxy-4-oxo-1,2,3-benzotriazine
DIC=1,3-Diisopropyl carbodiimide
DCC=1,3-Dicyclohexyl carbodiimide
DIEA=N,N-diisopropylethylamine
DIPEA=N,N-diisopropylethylamine
DMA=N,N-dimethylacetamide
DMAP=4-(N,N-dimethylamino)pyridine
DMF=N,N-dimethylformamide
DMF=N,N-dimethylformamide
DMPU=NN'-dimethylpropyleneurea, 1,3-dimethyl-2-oxo-hexahydropyrimidine
EDAC=1-(3-Dimethylaminopropyl)-3-ethyl-carbodiimide hydrochloride
$Et_2O$=diethyl ether
EtOAc=ethyl acetate
HMPA=hexamethylphosphoric acid triamide
HOBt=N-Hydroxybenzotriazole
HOAt=7-Aza-1-Hydroxybenzotriazole
LAH, ($LiAlH_4$)=Lithiumaluminium hydride
LDA=lithium diisopropylamide
MeCN=acetonitrile
MeOH=methanol
NMP=N-methylpyrrolidin-2-one
NaH=Sodium Hydride
$NH_2OH$=Hydroxylamine
PyBroP=Bromotrispyrrolidinophosphonium hexafluorophosphate
TEA ($Et_3N$)=triethylamine
TFA=trifluoroacetic acid
THF=tetrahydrofuran
$CDCl_3$=deuterio chloroform
$CD_3OD$=tetradeuterio methanol
DMSO-$d_6$=hexadeuterio dimethylsulfoxide
NMR Proton NMR spectra were recorded at ambient temperature using a Brucker Avance DPX 200 (200 MHz), Brucker Avance DPX 300 (300 MHz) and Brucker Avance DPX 400 (400 MHz) with tetramethylsilane as an internal standard. Chemical shifts (δ) are given in ppm
HPLC-MS
The following instrumentation is used:
Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector
The instrument is controlled by HP Chemstation software.

The HPLC pump is connected to two eluent reservoirs containing:

| Method A: | 0.01% TFA in water |
| --- | --- |
| Method B: | 0.01% TFA in acetonitrile |

The analysis is performed at 40° C. by injecting an appropriate volume of the sample (preferably 1 μl) onto the column which is eluted with a gradient of acetonitrile.

The HPLC conditions, detector settings and mass spectrometer settings used are given in the following table.

| Column | Waters Xterra MS C-18 X 3 mm id 5 μm |
| --- | --- |
| Gradient | 5%-100% acetonitrile linear during 7.5 min at 1.5 mL/min |
| Detection | 210 nm (analogue output from DAD) ELS (analogue output from ELS) |
| MS | ionisation mode API-ES Scan 100-1000 amu step 0.1 amu |

After the DAD the flow is divided yielding approximately 1 mL/min to the ELS and 0.5 mL/min to the MS.

General

The following examples and general procedures refer to intermediate compounds and final products for general formula (I) identified in the specification and in the synthesis schemes.

The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General procedures A through G described herein.

The structures of the compounds are confirmed by either by nuclear magnetic resonance (NMR) and/or by HPLS-MS.

General Reaction Schemes

The compounds of formula (I) according to the invention wherein $R^1$, $R^2$, $R^3$ and $R^4$ are as defined in formula (I) can be prepared as outlined in Scheme 1 and Scheme 2. The starting material can be either commercial available compounds or compounds that can be prepared following procedures described in the literature or prepared as described in the relevant examples and general procedures.

In Scheme 1 a secondary amine of general structure (II) can be treated with phosgene or related analogue (for example triphosgene, carbonyl diimidazole etc) in a solvent such as tetrahydrofuran or dichloromethane. The product carbamoyl chloride (III) can be treated with the anion prepared via reaction of urea (IV) and sodium hydride (J. Org. Chem. 1973, 38, 3868) to give compounds of general formular (Ia).

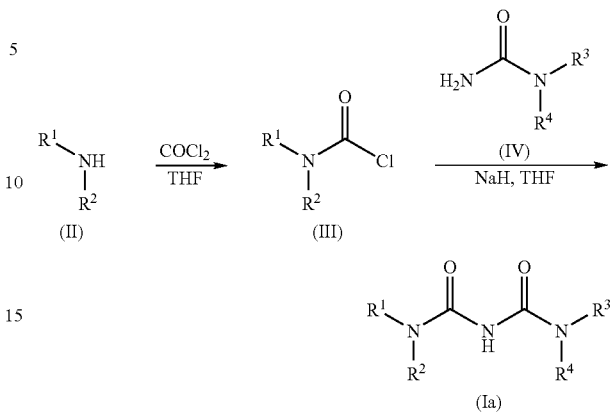

Scheme 1

In Scheme 2, chlorocarbonyl isocyanate can be treated sequentially with amines (II) and (VI) in a solvent such as tetrahydrofuran or dichloromethane to give compounds of general structure (I). (Tetrahedron 1993, 49, 3227).

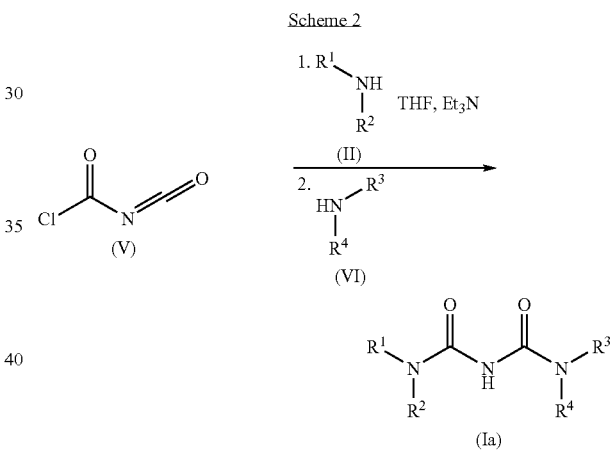

Scheme 2

General Procedures

General Procedure 1

To urea (IV) (Scheme 1) in tetrahydrofuran was added sodium hydride (1-3 equivalents) and the reaction mixture stirred for 50 min at room temp. The carbamoyl chloride (III) was then added (ice bath cooling used during addition) and the mixture was stirred overnight at room temperature. The reaction mixture was added to 0.5 ml water, partially concentrated in vacuo and water (2 mL) and ethyl acetate (10 mL) was added. The non soluble material was filtered off and the organic layer collected and concentrated in vacuo. The crude product was then dissolved in tetrahydrofuran and purified by chromatography to give the desired product (Ia) wherein $R^1$, $R^2$, $R^3$ and $R^4$ are as defined in formula (Ia).

General Procedure 2.

To compound (V) (Scheme 2) (commercially available) in tetrahydrofuran at −20-0° C. was added amine (II) and triethylamine. After 20 min amine (VI) was added and the reaction allowed to warm to room temperature over 3 h. The reaction mixture was partially concentrated. The crude product was then dissolved in tetrahydrofuran and purified by LCMS to the desired product (Ia) wherein $R^1$, $R^2$, $R^3$ and $R^4$ are as defined in formula (Ia).

Example 1

1,1-Bis-(cyclohexyl)-5-methyl biuret

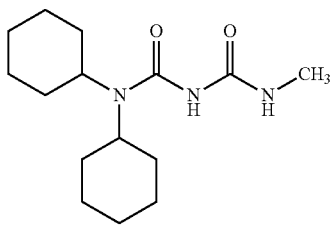

Prepared as described in General Procedure 1. To methyl urea (0.24 g) in tetrahydrofuran was added sodium hydride (22 mg of 60% in oil) and the reaction mixture stirred for 50 min at room temp. Dicyclohexyl carbamoyl chloride (0.8 g) was then added (ice bath cooling used during addition) and the mixture was stirred overnight. The reaction mixture was then added to 0.5 ml water, partially concentrated in vacuo and water (2 mL) and ethyl acetate (10 mL) was added. The non soluble material was removed by filtration and the organic layer collected and concentrated in vacuo. An aliquot of the crude was then dissolved in THF and purified by preparative LCMS to give the desired product (8 mg).

$^1$H NMR (CDCl$_3$): δ1.10-1.90 (m, 20H), 2.33 (d, 3H), 3.22-3.40 (m, 2H), 6.65 (s, 1H), 8.45 (s, 1H).

HPLC-MS: m/z=282.1 (M+1)

Example 2

1,1-Bis-(cyclohexyl)-5-butyl biuret

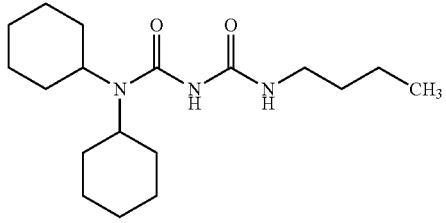

Prepared as described in General Procedure 1 using dicyclohexyl carbamoyl chloride and butyl urea.

HPLC-MS (Method A): m/z=324.2 (M+1)

Example 3

1,1-Bis-(cyclohexyl)-5-(3-pyridylmethyl) biuret

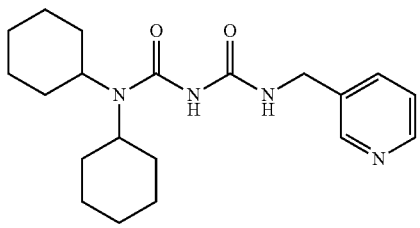

Prepared as described in General Procedure 1 using dicyclohexyl carbamoyl chloride and 1-(3-pyridylmethyl)urea.

HPLC-MS (Method B): m/z=359.2 (M+1)

Example 4

1,1-Bis-(cyclohexyl)-5-(4-fluorobenzyl) biuret

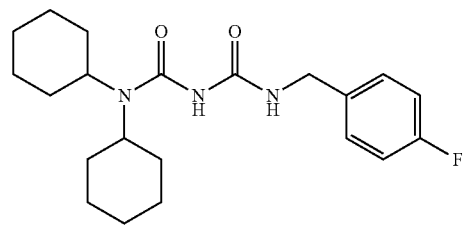

Prepared as described in General Procedure 1 using dicyclohexyl carbamoyl chloride and 4-fluorobenzyl urea.

HPLC-MS (Method A): m/z=376.2 (M+1)

Example 5

1,1-Bis-(cyclohexyl)-5-(3-chlorobenzyl) biuret

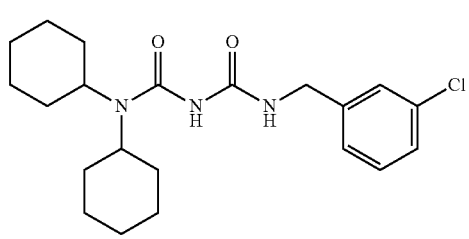

Prepared as described in General Procedure 1 using dicyclohexyl carbamoyl chloride and 3-chlorobenzyl urea.

HPLC-MS (Method A): m/z=392.2 (M+1)

Example 6

1,1-Bis-(cyclohexyl)-5-(o-tolyl) biuret

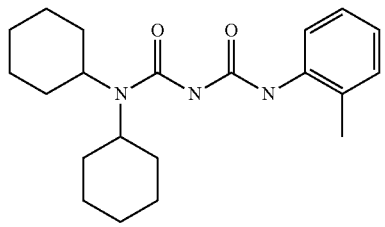

Prepared as described in General Procedure 1 using dicyclohexyl carbamoyl chloride and otolylurea.
HPLC-MS (Method A): m/z=358.2 (M+1)

Example 7

1,1-Bis-(cyclohexyl)-5-(2,2,2-trifluoroethyl) biuret

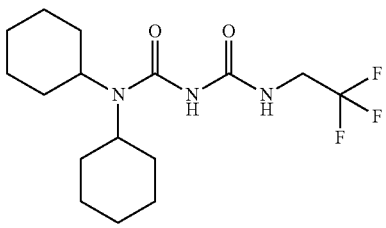

Prepared as described in General Procedure 1 using dicyclohexyl carbamoyl chloride and N-2,2,2-trifluoroethylurea.
HPLC-MS (Method A): m/z=350.1 (M+1)

Example 8

1,1-Bis-(cyclohexyl)-5-(2-thiazolyl) biuret

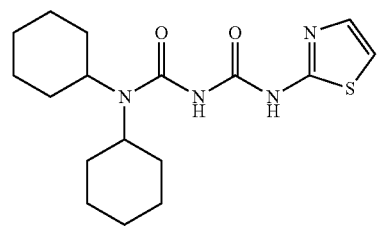

Prepared as described in General Procedure 2. To chlorocarbonyl isocyanate (0.2 g) in tetrahydrofuran at −20-0° C. was added dicyclohexylamine (1 equivalent) and triethylamine (0.27 mL). After 20 min 2-aminothiazole (0.2 g) was added and the reaction allowed to warm to room temperature over 3 h and stirred overnight at room temperature. The reaction mixture was partially concentrated. The crude product was then dissolved in tetrahydrofuran and purified by flash chromatography (Eluant 20 dichloromethane:1 methanol).
HPLC-MS (Method A): m/z=351.6 (M+1)

Example 9

1,1-Bis-(cyclohexyl)-5-ethyl biuret

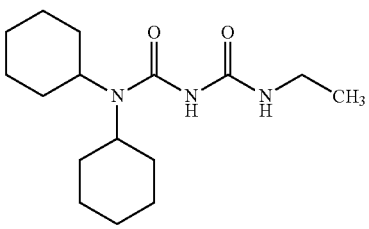

Prepared as described in General Procedure 2 using dicyclohexylamine and ethylamine.
HPLC-MS (Method A): m/z=296.7 (M+1)

Example 10

1,1-Bis-(cyclohexyl)-5-cyclopropyl biuret

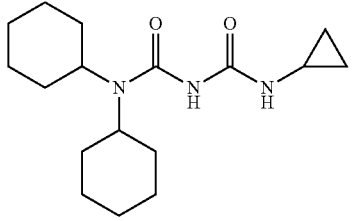

Prepared as described in General Procedure 2 using dicyclohexylamine and cyclopropylamine.
HPLC-MS (Method A): m/z=308.6 (M+1)

Example 11

1,1-Bis-(cyclohexyl)-5-(2-pyridylmethyl) biuret

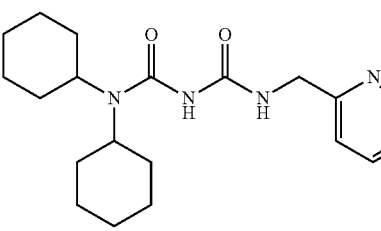

Prepared as described in General Procedure 2 using dicyclohexylamine and 2-(aminomethyl)pyridine.
HPLC-MS (Method A): m/z=359.7(M+1)

Example 12

1,1-Bis-(cyclohexyl)-5-(4-methoxybenzyl) biuret

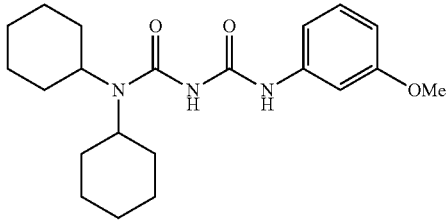

Prepared as described in General Procedure 2 using dicyclohexylamine and 4-methoxybenzylamine.

HPLC-MS (Method A): m/z=388.6 (M+1)

Example 13

1,1-Bis-(cyclohexyl)-5-(2-pyridyl) biuret

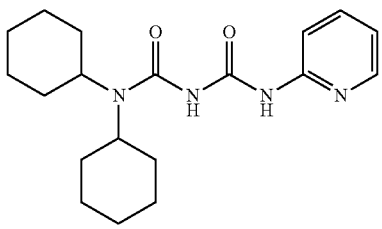

Prepared as described in General Procedure 2 using dicyclohexylamine and 2-aminopyridine.

HPLC-MS (Method A): m/z=345.5 (M+1)

Example 14

1,1-Bis-(cyclohexyl)-5-(2-thiazolyl-5-sulfanyl-acetic acid) biuret

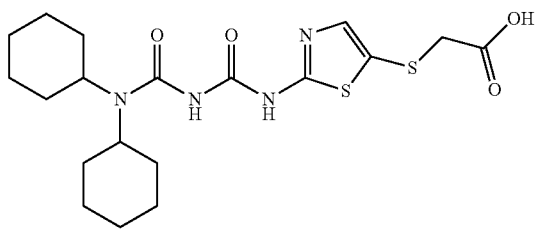

1,1-Bis-(cyclohexyl)-5-(2-thiazolyl-5-sulfanyl-acetic acid ethyl ester) biuret was prepared as described in General Procedure 2 and 3 using chlorocarbonyl isocyanate, dicyclohexylamine and 2-aminothiazole-5-sulfanylacetic acid ethyl ester. Ester hydrolysis using sodium hydroxyide (1N) in methanol at room temperature afforded the title compound.

HPLC-MS (Method A): m/z=441, $R_t$=2.29 min

Example 15

1-(trans-4-Methylcyclohexyl)-1-isobutyl-5-(2-thiazolyl-5-sulfanyl-acetic acid) biuret

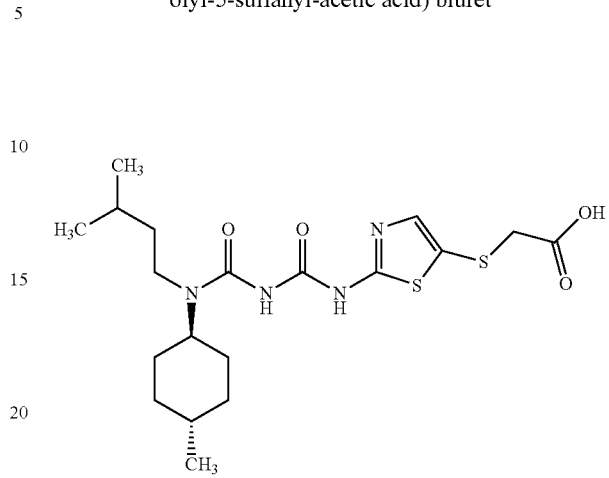

The title compound was prepared in a similar manner as described for 1,1-bis-(cyclohexyl)-5-(2-thiazolyl-5-sulfanyl-acetic acid) biuret using 1-(trans-4-methylcyclohexyl)-1-isobutylamine, 2-aminothiazole-5-sulfanylacetic acid ethyl ester and chlorocarbonyl isocyanate.

HPLC-MS (Method A): m/z=433, $R_t$=2.35 min

Example 16

1-(trans-Methylcyclohexyl)-1-cyclohexyl-5-(2-thiazolyl-5-sulfanyl-acetic acid) biuret

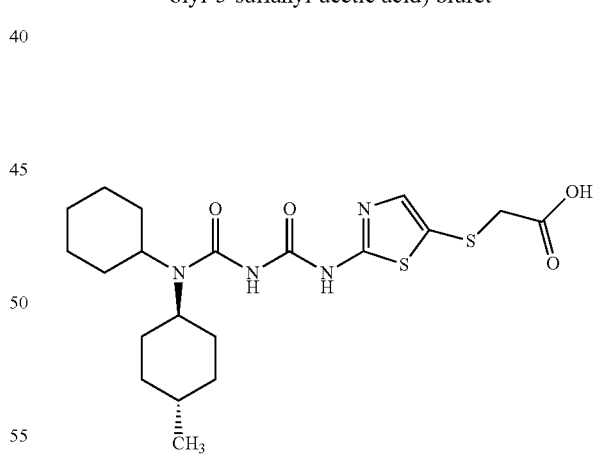

The title compound was prepared in a similar manner as described for 1,1-bis-(cyclohexyl)-5-(2-thiazolyl-5-sulfanyl-acetic acid) biuret using cyclohexyl-(4-trans-methyl-cyclohexyl)-amine, 2-aminothiazole-5-sulfanylacetic acid ethyl ester and chlorocarbonyl isocyanate.

HPLC-MS (Method A): m/z=455, $R_t$=2.43 min

Example 17

1-(trans-Propyloxycyclohexyl)-1-cyclohexyl-5-(2-thiazolyl-5-sulfanl-acetic acid) biuret

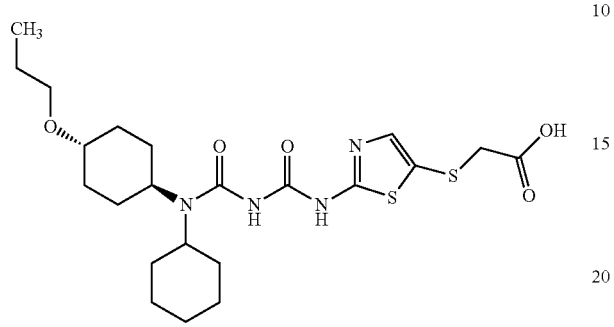

The title compound was prepared in a similar manner as described for 1,1-bis-(cyclohexyl)-5-(2-thiazolyl-5-sulfanyl-acetic acid) biuret using 1-(trans-4-ethyloxycyclohexyl)-1-cyclohexylamine, 2-aminothiazole-5-sulfanylacetic acid ethyl ester and chlorocarbonyl isocyanate.

HPLC-MS (Method A): m/z=499, $R_t$=2.28 min

Example 18

1-(trans-4-Methylcyclohexyl)-1-butyl-5-(2-thiazolyl-5-sulfanyl-acetic acid) biuret

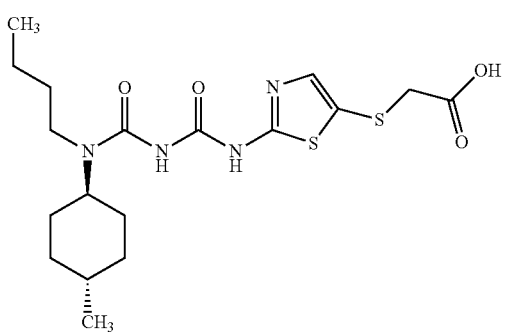

The title compound was prepared in a similar manner as described for 1,1-bis-(cyclohexyl)-5-(2-thiazolyl-5-sulfanyl-acetic acid) biuret using 1-(trans-4-methylcyclohexyl)-1-butylamine, 2-aminothiazole-5-sulfanylacetic acid ethyl ester and chlorocarbonyl isocyanate.

HPLC-MS (Method A): m/z=429, $R_t$=2.24 min

Example 19

1-(trans-4-Methylcyclohexyl)-1-cyclohexyl-5-(propionic acid) biuret

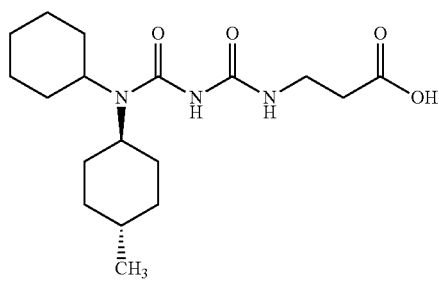

The title compound was prepared in a similar manner as described for 1,1-bis-(cyclohexyl)-5-(2-thiazolyl-5-sulfanyl-acetic acid) biuret using cyclohexyl-(4-trans-methyl-cyclohexyl)-amine, 3-amino propionic acid ethyl ester and chlorocarbonyl isocyanate.

HPLC-MS (Method A): m/z=354, $R_t$=2.03 min

Example 20

1-(trans-4-Methylcyclohexyl)-1-cyclohexylmethyl-5-(2-thiazolyl-5-sulfanyl-acetic acid) biuret

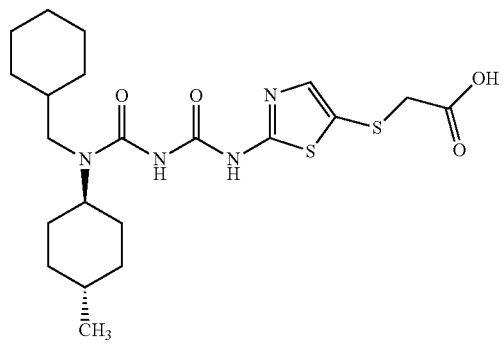

The title compound was prepared in a similar manner as described for 1,1-bis-(cyclohexyl)-5-(2-thiazolyl-5-sulfanyl-acetic acid) biuret using 1-(trans-4-methylcyclohexyl)-1-cyclohexylmethylamine, 2-aminothiazole-5-sulfanylacetic acid ethyl ester and chlorocarbonyl isocyanate.

HPLC-MS (Method A): m/z=469, $R_t$=1.39 min

Example 21

1-(trans-4-Methylcyclohexyl)-1-cyclopentylmethyl5-(2-thiazolyl-5-sulfanyl-acetic acid) biuret

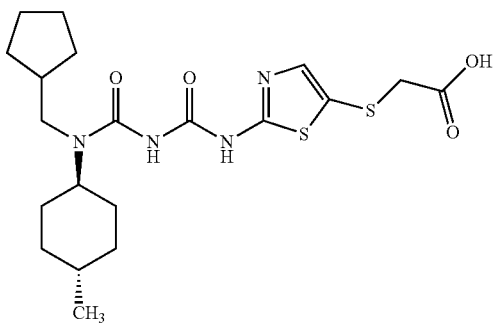

The title compound was prepared in a similar manner as described for 1,1-bis-(cyclohexyl)-5-(2-thiazolyl-5-sulfanyl-acetic acid) biuret using 1-(trans-4-methylcyclohexyl)-1-cyclopentylmethylamine, 2-aminothiazole-5-sulfanylacetic acid ethyl ester and chlorocarbonyl isocyanate HPLC-MS (Method A): m/z=368, $R_t$=2.09 min

Example 22

1-(trans-4-Methylcyclohexyl)-1-cyclohexyl-5-(butanoic acid) biuret

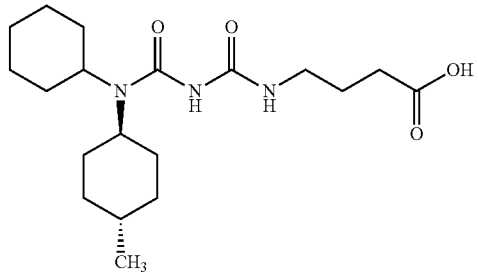

The title compound was prepared in a similar manner as described for 1,1-bis-(cyclohexyl)-5-(2-thiazolyl-5-sulfanyl-acetic acid) biuret using cyclohexyl-(4-trans-methyl-cyclohexyl)-amine, 4-aminobutanoic acid ethyl ester and chlorocarbonyl isocyanate.

HPLC-MS (Method A): m/z=368, $R_t$=2.09 min

Example 23

1-(trans-4-Methylcyclohexyl)-1-cyclohexyl-5-(1-trifluoromethyl-propionic acid) biuret

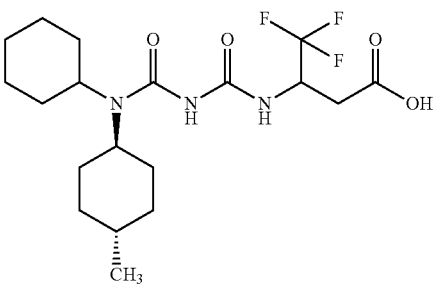

The title compound was prepared in a similar manner as described for 1,1-bis-(cyclohexyl)-5-(2-thiazolyl-5-sulfanyl-acetic acid) biuret using cyclohexyl-(4-trans-methyl-cyclohexyl)-amine, 3-amino-2-trifluoropropionic acid ethyl ester and chlorocarbonyl isocyanate.

HPLC-MS (Method A): m/z=422, $R_t$=2.30 min

Example 24

1-(trans-4-Methylcyclohexyl)-1-cyclohexyl-5-(methyl-4-carboxybenzoic acid) biuret

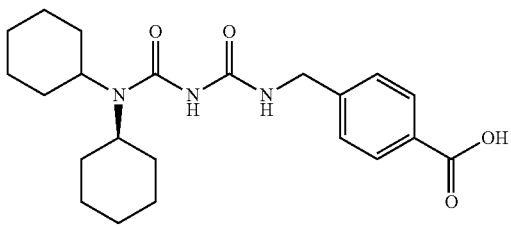

The title compound was prepared in a similar manner as described for 1,1-bis-(cyclohexyl)-5-(2-thiazolyl-5-sulfanyl-acetic acid) biuret using cyclohexyl-(4-trans-methyl-cyclohexyl)-amine, 4-aminomethyl-benzoic acid ethyl ester and chlorocarbonyl isocyanate.

HPLC-MS (Method A): m/z=416, $R_t$=2.31 min

Example 25

1-(trans-4-Methylcyclohexyl)-1-cyclohexyl-5-(trans-4-carboxycyclohexylmethyl) biuret

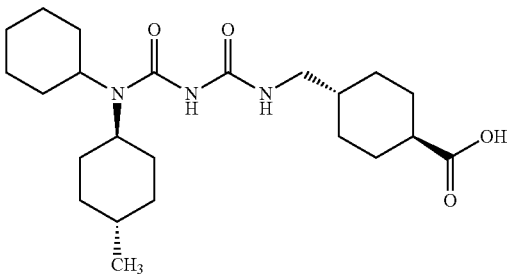

The title compound was prepared in a similar manner as described for 1,1-bis-(cyclohexyl)-5-(2-thiazolyl-5-sulfanyl-acetic acid) biuret using cyclohexyl-(4-trans-methyl-cyclohexyl)-amine, 4-aminomethyl-cyclohexanoic acid ethyl ester and chlorocarbonyl isocyanate.

HPLC-MS (Method A): m/z=422, $R_t$=2.31 min

Example 26

1-(trans-4-Methylcyclohexyl)-1-cyclohexyl-5-(pyrrolidone-N-propyl)) biuret

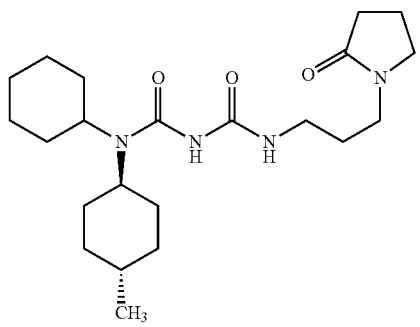

The title compound was prepared in a similar manner as described in General Procedure 2 using cyclohexyl-(4-trans-methyl-cyclohexyl)-amine, aminopropylpyrrolidine and chlorocarbonyl isocyanate.

HPLC-MS (Method A): m/z=407, $R_t$=2.10 min

The invention claimed is:
1. A compound of formula (I)

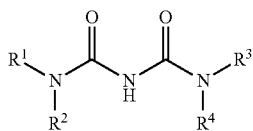

wherein $R^1$ is $C_{1-6}$-alkyl, $C_{3-8}$-cycloalkyl, $C_{3-8}$-cycloalkyl-$C_{1-6}$-alkyl, $C_{3-8}$-cycloalkenyl, $C_{3-8}$-heterocyclyl, $C_{3-8}$-heterocycloalkenyl, fused aryl-$C_{3-8}$-cycloalkyl, or fused heteroaryl-$C_{3-8}$-cycloalkyl, each of which is optionally substituted with one or more substituents $R^5$, $R^6$, $R^7$ and $R^8$;

$R^2$ is $C_{3-8}$-cycloalkyl, $C_{3-8}$-cycloalkenyl, $C_{3-8}$-heterocyclyl, $C_{3-8}$-heterocycloalkenyl, fused aryl-$C_{3-8}$-cycloalkyl or fused heteroaryl-$C_{3-8}$-cycloalkyl, each of which is optionally substituted with one or more substituents $R^9$, $R^{10}$, $R^{11}$ and $R^{12}$;

$R^3$ is hydrogen, $C_{1-6}$-alkyl, $C_{2-6}$-alkenyl, $C_{2-6}$-alkynyl, $C_{3-8}$-cycloalkyl, $C_{3-8}$-heterocyclyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy-$C_{1-6}$-alkyl, aryloxy-$C_{1-6}$-alkyl, heteroaryloxy-$C_{1-6}$-alkyl, $C_{3-6}$-cycloalkyl-$C_{1-6}$-alkoxy-$C_{1-6}$-alkyl, aryl-$C_{1-6}$-alkoxy-$C_{1-6}$-alkyl, heteroaryl, $C_{1-6}$-alkyl-C(O)—O—$C_{1-6}$-alkyl, $C_{1-6}$-alkylthio-$C_{1-6}$-alkyl, amino-$C_{1-6}$-alkyl, $C_{1-6}$-alkylamino-$C_{1-6}$-alkyl, di-($C_{1-6}$-alkyl)amino$C_{1-6}$-alkyl each of which is optionally substituted with one or more substituents independently selected from $R^{20}$;

$R^4$ is thiazolyl which is optionally substituted with one or more substituents independently selected from $R^{21}$;

$R^5$, $R^6$, $R^7$, $R^8$, $R^9$, $R^{10}$, $R^{11}$ and $R^{12}$ are independently selected from the group consisting of halogen, nitro, cyano, hydroxy, oxo, carboxy, —$CF_3$; or —$NR^{13}R^{14}$; or $C_{1-6}$-alkyl, $C_{2-6}$-alkenyl, $C_{2-6}$-alkynyl, $C_{3-8}$-cycloalkyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy, $C_{3-6}$-cycloalkyl-$C_{1-6}$-alkoxy, aryl-$C_{1-6}$-alkoxy, aryloxy-$C_{1-6}$-alkyl, $C_{3-6}$-cycloalkyl-$C_{1-6}$-alkoxy-$C_{1-6}$-alkyl, $C_{1-6}$-alkoxy-$C_{1-6}$-alkyl, aryl-$C_{1-6}$-alkoxy-$C_{1-6}$-alkyl, heteroaryl, heteroaryl-$C_{1-6}$-alkoxy, aryloxy, heteroaryloxy, $C_{3-6}$-cycloalkyl-$C_{1-6}$-alkylthio, $C_{1-6}$-alkyl-C(O)—O—$C_{1-6}$-alkyl, $C_{1-6}$-alkylthio-$C_{1-6}$-alkyl, carboxy-$C_{1-6}$-alkyloxy, amino-$C_{1-6}$-alkyl, $C_{1-6}$-alkylamino-$C_{1-6}$-alkyl, di-($C_{1-6}$-alkyl)amino-$C_{1-6}$-alkyl each of which is optionally substituted with one or more substituents independently selected from $R^{15}$; or —C(O)—$R^{16}$, —S(O)$_2$—$R^{16}$, —C(O)—$NR^{17}R^{18}$, —S(O)$_2$—$NR^{17}R^{18}$, —$C_{1-6}$-alkyl-C(O)—$NR^{17}R^{18}$; or $R^{13}$ and $R^{14}$ independently represent hydrogen, $C_{1-6}$-alkyl, —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —S(O)$_2$—$C_{1-6}$-alkyl, or aryl, each of which is optionally substituted with one or more halogens;

$R^{15}$ is halogen, cyano, carboxy, hydroxy, —C(O)—O—$C_{1-6}$-alkyl, —$CF_3$, $C_{1-6}$-alkyl, $C_{1-6}$-alkoxy, —$NR^{10}R^{11}$, —S(O)$_2CH_3$, S(O)$_2CH_2CF_3$, —S(O)$_2CF_3$, or —S(O)$_2NH_2$;

$R^{16}$ is $C_{1-6}$-alkyl, $C_{1-6}$-alkoxy, $C_{2-6}$-alkenyl, $C_{2-6}$-alkynyl, $C_{3-8}$-cycloalkyl, $C_{3-8}$-cycloalkyl-$C_{1-6}$-alkyl, aryl, aryl-$C_{1-6}$-alkyl, aryloxy-$C_{1-6}$-alkyl, heteroaryl, $C_{3-8}$-heterocyclyl, heteroaryl-$C_{1-6}$-alkyl, $C_{3-8}$-heterocyclyl-$C_{1-6}$-alkyl, heteroaryloxy-$C_{1-6}$-alkyl, carboxy-$C_{1-6}$-alkyl, carboxy-$C_{2-6}$-alkenyl, $C_{1-6}$-alkoxy-$C_{1-6}$-alkyl, $C_{1-6}$-alkoxy-$C_{2-6}$-alkenyl, $R^{13}$HN—$C_{1-6}$-alkyl, $R^{13}R^{14}$—N—$C_{1-6}$-alkyl, $R^{13}R^{14}$—N—$C_{2-6}$-alkenyl, $R^{13}R^{14}$—N—S(O)$_2$—$C_{1-6}$-alkyl, $R^{13}R^{14}$—N—C(O)—$C_{1-6}$-alkyl, $C_{1-6}$-alkyl-C(O)—NH—$C_{1-6}$-alkyl, aryl-C(O)—NH—$C_{1-6}$-alkyl, heteroaryl-C(O)—NH—$C_{1-6}$-alkyl, $C_{3-8}$-cycloalkyl-C(O)—NH—$C_{1-6}$-alkyl each of which is optionally substituted with one or more substituents independently selected from $R^{15}$;

$R^{17}$ and $R^{18}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{19}$; or $R^{17}$ and $R^{18}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{19}$ is halogen, cyano, hydroxy, carboxy, —$CF_3$, $C_{1-6}$-alkyl, —$S(O)_2CH_3$, or —$S(O)_2NH_2$;

$R^{20}$ and $R^{21}$ are independently selected from the group consisting of halogen, hydroxy, carboxy, oxo, —$CF_3$, carboxy-$C_{1-6}$-alkyl, hydroxy-$C_{1-6}$-alkyl, carboxy-$C_{1-6}$-alkylthio, carboxy-$C_{2-6}$-alkenylthio, carboxy-$C_{1-6}$-alkylsulfonyl, carboxy-$C_{1-6}$-alkylsulfamoyl, $C_{1-6}$-alkoxy, alkylamino, —C(O)—$C_{1-6}$-alkyl;

or a pharmaceutically acceptable salt thereof.

2. A compound according to claim 1, wherein
$R^1$ is $C_{3-8}$-cycloalkyl, $C_{3-8}$-cycloalkyl-$C_{1-6}$-alkyl, or $C_{3-8}$-heterocyclyl, each of which is optionally substituted with one or more substituents $R^5$, $R^6$, $R^7$ and $R^8$;

$R^2$ is $C_{3-8}$-cycloalkyl or $C_{3-8}$-heterocyclyl, each of which is optionally substituted with one or more substituents $R^9$, $R^{10}$, $R^{11}$ and $R^{12}$;

$R^3$ is hydrogen, $C_{1-6}$-alkyl, $C_{2-6}$-alkenyl, $C_{2-6}$-alkynyl, $C_{3-8}$-cycloalkyl, $C_{3-8}$-heterocyclyl, $C_{3-6}$-cycloalkyl-$C_{1-6}$-alkyl, aryl, aryl-$C_{1-6}$-alkyl, heteroaryl-$C_{1-6}$-alkyl, $C_{1-6}$-alkoxy-$C_{1-6}$-alkyl, aryloxy-$C_{1-6}$-alkyl, heteroaryloxy-$C_{1-6}$-alkyl, $C_{3-6}$-cycloalkyl-$C_{1-6}$-alkoxy-$C_{1-6}$-alkyl, aryl-$C_{1-6}$-alkoxy-$C_{1-6}$-alkyl, heteroaryl, $C_{1-6}$-alkyl-C(O)—O—$C_{1-6}$-alkyl, $C_{1-6}$-alkylthio-$C_{1-6}$-alkyl, amino-$C_{1-6}$-alkyl, $C_{1-6}$-alkylamino-$C_{1-6}$-alkyl, di-($C_{1-6}$-alkyl)amino-$C_{1-6}$-alkyl each of which is optionally substituted with one or more substituents independently selected from $R^{20}$;

$R^5$, $R^6$, $R^7$, $R^8$, $R^9$, $R^{10}$, $R^{11}$ and $R^{12}$ are independently selected from the group consisting of
$C_{1-6}$-alkyl, halogen, nitro, cyano, hydroxy, oxo, carboxy, —$CF_3$; or
—$NR^{13}R^{14}$; or
$C_{1-6}$-alkoxy, $C_{3-6}$-cycloalkyl-$C_{1-6}$-alkoxy, aryl-$C_{1-6}$-alkoxy, aryloxy-$C_{1-6}$-alkyl, $C_{3-6}$-cycloalkyl-$C_{1-6}$-alkoxy-$C_{1-6}$-alkyl, $C_{1-6}$-alkoxy-$C_{1-6}$-alkyl, aryl-$C_{1-6}$-alkoxy-$C_{1-6}$-alkyl, heteroaryl, heteroaryl-$C_{1-6}$-alkoxy, aryloxy, heteroaryloxy, each of which is optionally substituted with one or more substituents independently selected from $R^{15}$; or
—C(O)—$R^{16}$, —$S(O)_2$—$R^{16}$, —C(O)—$NR^{17}R^{18}$, —$S(O)_2$—$NR^{17}R^{18}$, —$C_{1-6}$-alkyl-C(O)—$NR^{17}R^{18}$; or $R^{13}$ and $R^{14}$ independently represent —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —$S(O)_2$—$C_{1-6}$-alkyl, each of which is optionally substituted with one or more halogens;

$R^{15}$ is halogen, carboxy, or $C_{1-6}$-alkoxy;

$R^{16}$ is $C_{1-6}$-alkyl, $C_{1-6}$-alkoxy, aryloxy-$C_{1-6}$-alkyl, carboxy-$C_{1-6}$-alkyl, carboxy-$C_{2-6}$-alkenyl, or $C_{1-6}$-alkoxy-$C_{1-6}$-alkyl, each of which is optionally substituted with one or more substituents independently selected from $R^{15}$;

$R^{17}$ and $R^{18}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{19}$; or $R^{17}$ and $R^{18}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{19}$ is halogen, cyano, hydroxy, carboxy, —$CF_3$, $C_{1-6}$-alkyl, —$S(O)_2CH_3$, or —$S(O)_2NH_2$;

$R^{20}$ and $R^{21}$ are independently selected from the group consisting of halogen, carboxy, oxo, carboxy-$C_{1-6}$-alkyl, —$CF_3$, hydroxy-$C_{1-6}$-alkyl, carboxy-$C_{1-6}$-alkylthio, carboxy-$C_{2-6}$-alkenylthio, carboxy-$C_{1-6}$-alkylsulfonyl, carboxy-$C_{1-6}$-alkylsulfamoyl, $C_{1-6}$-alkoxy, alkylamino, —C(O)—$C_{1-6}$-alkyl;

or a pharmaceutically acceptable salt thereof.

3. A compound according to claim 2, wherein
$R^1$ is cyclopentyl, cyclohexyl, cycloheptyl, cyclohexylmethyl, or piperidinyl, each of which is optionally substituted with one or more substituents $R^5$, $R^6$, $R^7$ and $R^8$;

$R^2$ is cyclopentyl, cyclohexyl, cycloheptyl, or piperidinyl, each of which is optionally substituted with one or more substituents $R^9$, $R^{10}$, $R^{11}$ and $R^{12}$;

$R^3$ is hydrogen, $C_{1-6}$-alkyl, $C_{3-8}$-cycloalkyl, $C_{3-8}$-heterocyclyl, aryl, aryl-$C_{1-6}$-alkyl, heteroaryl-$C_{1-6}$-alkyl, heteroaryloxy-$C_{1-6}$-alkyl, heteroaryl, or $C_{1-6}$-alkylthio-$C_{1-6}$-alkyl, each of which is optionally substituted with one or more substituents independently selected from $R^{20}$;

$R^5$, $R^6$, $R^7$, $R^8$, $R^9$, $R^{10}$, $R^{11}$ and $R^{12}$ are independently selected from the group consisting of
$C_{1-6}$-alkyl, halogen, nitro, cyano, hydroxy, oxo, carboxy, —$CF_3$; or
—$NR^{13}R^{14}$; or
$C_{1-6}$-alkoxy, $C_{3-6}$-cycloalkyl-$C_{1-6}$-alkoxy, aryl-$C_{1-6}$-alkoxy, aryloxy-$C_{1-6}$-alkyl, $C_{3-6}$-cycloalkyl-$C_{1-6}$-alkoxy-$C_{1-6}$-alkyl, $C_{1-6}$-alkoxy-$C_{1-6}$-alkyl, aryl-$C_{1-6}$-alkoxy-$C_{1-6}$-alkyl, heteroaryl, heteroaryl-$C_{1-6}$-alkoxy, aryloxy, heteroaryloxy, each of which is optionally substituted with one or more substituents independently selected from $R^{15}$; or
—C(O)—$R^{16}$, —$S(O)_2$—$R^{16}$, —C(O)—$NR^{17}R^{18}$, —$S(O)_2$—$NR^{17}R_{18}$, —$C_{1-6}$-alkyl-C(O)—$NR^{17}R^{18}$; or $R^{13}$ and $R^{14}$ independently represent —C(O)—$C_{1-6}$-alkyl, —C(O)—O—$C_{1-6}$-alkyl, carboxy-$C_{1-6}$-alkyl, —C(O)—$C_{1-6}$-alkyl-C(O)OH, —$S(O)_2$—$C_{1-6}$-alkyl, each of which is optionally substituted with one or more halogens;

$R^{15}$ is halogen, carboxy, or $C_{1-6}$-alkoxy;

$R^{16}$ is $C_{1-6}$-alkyl, $C_{1-6}$-alkoxy, aryloxy-$C_{1-6}$-alkyl, carboxy-$C_{1-6}$-alkyl, carboxy-$C_{2-6}$-alkenyl, or $C_{1-6}$-alkoxy-$C_{1-6}$-alkyl, each of which is optionally substituted with one or more substituents independently selected from $R^{15}$;

$R^{17}$ and $R^{18}$ are independently selected from the group consisting of hydrogen, $C_{1-6}$-alkyl, hydroxy-$C_{1-6}$-alkyl, carboxy-$C_{1-6}$-alkyl, aryl, or heteroaryl, each of which is optionally substituted with one or more substituents independently selected from $R^{19}$; or $R^{17}$ and $R^{18}$ together with the nitrogen to which they are attached form a 3 to 8 membered heterocyclic ring with the said nitrogen atom, the heterocyclic ring optionally containing one or two further heteroatoms selected from nitrogen, oxygen and sulphur;

$R^{19}$ is halogen, cyano, hydroxy, carboxy, —$CF_3$, $C_{1-6}$-alkyl, —$S(O)_2CH_3$, or —$S(O)_2NH_2$;

$R^{20}$ and $R^{21}$ are independently selected from the group consisting of halogen, carboxy, oxo, —$CF_3$, carboxy-$C_{1-6}$-alkyl, hydroxy-$C_{1-6}$-alkyl, carboxy-$C_{1-6}$-alkylthio, carboxy-$C_{2-6}$-alkenylthio, carboxy-$C_{1-6}$-alkylsulfonyl, carboxy-$C_{1-6}$-alkylsulfamoyl, $C_{1-6}$-alkoxy, alkylamino, —C(O)—$C_{1-6}$-alkyl;

or a pharmaceutically acceptable salt thereof.

4. A compound according to claim 3 wherein $R^{21}$ is halogen or carboxy-$C_{1-6}$-alkylthio.

5. A compound according to claim 3 wherein $R^5$, $R^6$, $R^7$, $R^8$, $R^9$, $R^{10}$, $R^{11}$ and $R^{12}$ are independently selected from $C_{1-6}$-alkyl.

6. A compound according to claim 1 selected from the following:

- 1,1-Bis-(cyclohexyl)-5-(2-thiazolyl) biuret;
- 1,1-Bis-(cyclohexyl)-5-(2-thiazolyl-5-sulfanyl-acetic acid) biuret;
- 1-(trans-4-Methylcyclohexyl)-1-isobutyl-5-(2-thiazolyl-5-sulfanyl-acetic acid) biuret;
- 1-(trans-Methylcyclohexyl)-1-cyclohexyl-5-(2-thiazolyl-5-sulfanyl-acetic acid) biuret;
- 1-(trans-Propyloxycyclohexyl)-1-cyclohexyl-5-(2-thiazolyl-5-sulfanyl-acetic acid) biuret;
- 1-(trans-4-Methylcyclohexyl)-1-butyl-5-(2-thiazolyl-5-sulfanyl-acetic acid) biuret;
- 1-(trans-4-Methylcyclohexyl)-1-cyclohexylmethyl-5-(2-thiazolyl-5-sulfanyl-acetic acid) biuret; and
- 1-(trans-4-Methylcyclohexyl)-1-cyclopentylmethyl5-(2-thiazolyl-5-sulfanyl-acetic acid) biuret;

or a pharmaceutically acceptable salt thereof.

7. A pharmaceutical composition, comprising: a pharmaceutically acceptable carrier and a compound of claim 1, or a pharmaceutically acceptable salt thereof.

* * * * *